United States Patent [19]

Bühler et al.

[11] 4,420,308
[45] Dec. 13, 1983

[54] PROCESS FOR THE PRODUCTION OF RESERVE EFFECTS ON POLYESTER TEXTILES AND POLYESTER/CELLULOSE MIXED FIBRE TEXTILES: DISCHARGE PRINTING WITH DISPERSE AZO DYE WITH ALKYL OR ALKOXY CARBONYL, CYAND AND HYDROXY PHENYL GROUP

[75] Inventors: Ulrich Bühler, Schöneck; Horst Kindler, Frankfurt; Klaus Kühlein, Kelkheim; Maria Kallay, Königstein; Uwe Kosubek, Büttelborn; Rudolf Löwenfeld, Dreieich; Kurt Roth, Hofheim, all of Fed. Rep. of Germany

[73] Assignee: Cassella Aktiengesellschaft, Frankfurt am Main, Fed. Rep. of Germany

[21] Appl. No.: 384,074

[22] Filed: Jun. 1, 1982

[30] Foreign Application Priority Data

Sep. 8, 1981 [DE] Fed. Rep. of Germany ....... 3135433

[51] Int. Cl.³ .......................... C09B 29/01; D06P 5/12
[52] U.S. Cl. ............................. 8/464; 8/532; 8/922
[58] Field of Search ............................ 8/464, 463, 532

[56] References Cited

U.S. PATENT DOCUMENTS

| 4,252,530 | 2/1981 | Ribka et al. | 8/662 |
| 4,265,629 | 5/1981 | Ribka et al. | 8/464 |
| 4,322,213 | 3/1982 | Tappe et al. | 8/449 |

FOREIGN PATENT DOCUMENTS

| 41697 | 6/1981 | European Pat. Off. . |
| 3016301 | 10/1981 | Fed. Rep. of Germany . |
| 1543724 | 4/1979 | United Kingdom . |
| 2071707 | 9/1981 | United Kingdom . |
| 2071708 | 9/1981 | United Kingdom . |
| 2073230 | 10/1981 | United Kingdom . |

OTHER PUBLICATIONS

Research Disclosure, vol. 198, Oct. 1980, pp. 415-416, Nr. 19827, Havant, Hamsphire (GB); "A Process for the Discharge of Aromatic Polyester Textile Materials".

Primary Examiner—A. Lionel Clingman
Attorney, Agent, or Firm—Connolly and Hutz

[57] ABSTRACT

In a process known per se for the preparation of white patterns or patterns of various colors on a colored substrate on textile materials comprising hydrophobic synthetic fibres or on textile materials based on mixed fibres composed of polyester and cellulose comprising discharge printing wherein a discharge reserving agent based on an alkali or on sulphites, the improvement which comprises employing as the dischargeable disperse dyestuffs having the formula I

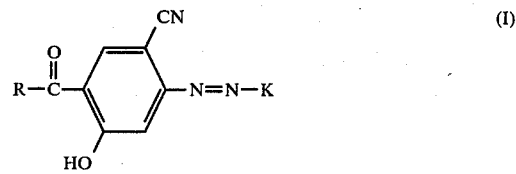

in which R and K have the meanings given in claim 1.

8 Claims, No Drawings

PROCESS FOR THE PRODUCTION OF RESERVE EFFECTS ON POLYESTER TEXTILES AND POLYESTER/CELLULOSE MIXED FIBRE TEXTILES: DISCHARGE PRINTING WITH DISPERSE AZO DYE WITH ALKYL OR ALKOXY CARBONYL, CYAND AND HYDROXY PHENYL GROUP

In the field of textile printing, it has always been a problem to poduce white or coloured patterns having sharp outlines on a dark-coloured background. Particularly if it is desired to produce filigree-like patterns on a dark substrate, direct printing of the textile material fails completely. It has been known for a long time to produce such designs by printing a discharge paste in the desired pattern on a deep background dyeing produced by means of a dyestuff dischargeable to white, and then to destroy, by means of a dry or wet heat treatment, the dyestuff on the areas which have been printed with the discharge paste. When the prints thus obtained have been washed out, the desired pattern is obtained in the form of white on a dark ground. It is also already known to add, to the discharge printing pastes, dyestuffs which are resistant to the discharging agent. In this case, the textile material is dyed on the printed areas by means of the indestructible dyestuff at the same time as the ground dyeing is destroyed. Coloured prints on a dark ground are obtained in this case. Coloured prints on a dark ground can also be obtained if the dark ground is produced using a mixture of a dischargeable dyestuff and a non-dischargeable dyestuff of another colour, by introducing both types of dyestuff into the padding liquor.

A process known from German Offenlegungsschrift No. 2,836,391 for producing discharge reserve prints on textile materials, particularly materials which contain hydrophobic fibres, preferably polyester fibres, to a predominant extent, or which consist of such fibres, by impregnating the materials with dye liquors which, besides customary dyeing and padding auxiliaries, contain dyestuffs which are dischargeable to white and, if appropriate, dyestuffs which are resistant to discharging agents, drying or incipiently drying the padded materials and then printing on a discharge reserve paste which, besides the discharging agent, also contains, if desired, dyestuffs which are resistant to discharging agents, and subsequently subjecting the material to a heat treatment at temperatures of 100° to 230° C. The dyestuffs dischargeable to white which are used are dyestuffs of the formula

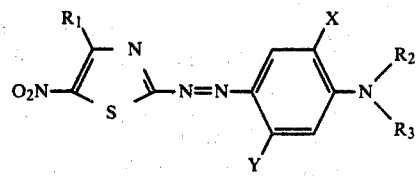

wherein $R_1$, $R_2$, X and Y denote hydrogen or a monovalent substituent and $R_3$ denotes a monovalent hydrocarbon radical. The discharging agents employed are bases which product a pH value of at least 8 in a 5% strength aqueous solution, such as, for example, hydroxides of the alkali and alkaline earth metals, salts of alkaline earth and alkali metals with weak organic or inorganic acids, ammonia or aliphatic amines. The base preferably used in the discharge reserve printing pastes is sodium hydroxide, carbonate or bicarbonate or potassium hydroxide, carbonate or bicarbonate.

It is known from German Offenlegungsschrift No. 2,856,283 to produce reserve effects on textile materials based on mixed fibres composed of polyester and cellulose, in particular polyester/cotton fibres, by impregnating the materials with dye liquors which, besides customary dyeing and padding auxiliaries, contain disperse by dyestuffs and reactive dyestuffs which react with the reserving agents and which, if appropriate, contain further disperse dyestuffs and reactive dyestuffs which are stable to the reserving agents, drying or incipiently drying the padded materials and then printing on a reserve paste which, besides the reserving agent, contains, if desired, disperse dyestuffs and reactive dyestuffs which are stable to the reserving agent, subjecting the material to a heat treatment at temperatures of 100° to 190° C. and then fixing the reactive dyestuff by alkali in a manner which is in itself known. In this known process, the dischargeable disperse dyestuffs employed are also dyestuffs of the formula

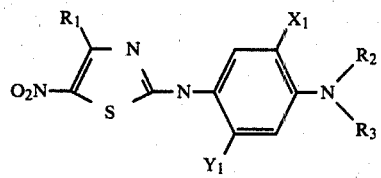

wherein $R_1$, $R_2$, $X_1$ and $Y_1$ denote hydrogen or a monovalent substituent and $R_3$ denotes a monovalent hydrocarbon radical, or dyestuffs of the formula

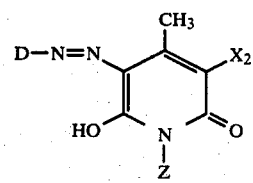

wherein D represents phenyl which optionally contains at least one substituent; $X_2$ denotes hydrogen or a monovalent substituent and Z denotes hydrogen or a monovalent hydrocarbon radical. The dischargeable reactive dyestuffs used in this case are dyestuffs which contain reactive radicals of the following formulae:

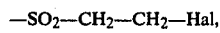

—SO$_2$—CH$_2$—CH$_2$—Hal,

—SO$_2$—CH$_2$—CH$_2$—O—SO$_3$M,

—NH—SO$_2$—CH$_2$—CH$_2$—O—SO$_3$M and

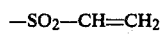

—SO$_2$—CH=CH$_2$ wherein M denotes hydrogen or a metal cation and Hal denotes halogen. The reserve paste employed in this process contains, as the reserving agent (a) an alkali metal sulphite or an alkali metal bisulphite in combination with an alkali metal carbonate or bicarbonate and, if appropriate, an aldehyde, and (b), if appropriate, a nonionic detergent.

It is known from German Offenlegungsschrift No. 3,019,726 that very good reserve effects are also obtained on the said textile materials by the process of German Offenlegungsschrift No. 2,856,283 if the dischargeable disperse dyestuffs employed are dyestuffs of the formula

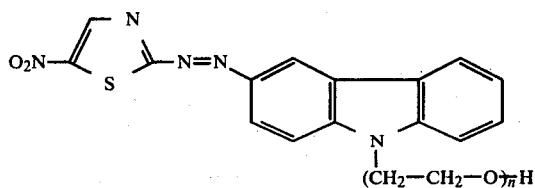

wherein n denotes a number from 1 to 9, preferably 1 to 5.

It can be inferred from British patent application Nos. 2,071,707 and 2,071,708 that, when the known discharge reserve printing processes are carried out "wet on wet'-'—for example if incipient drying is only carried out for a short time or not at all in the processes of German Offenlegungsschrift No. 2,836,391 or No. 2,856,283—it is advantageous to employ sodium silicate or potassium silicate as the substance having an alkaline reaction.

It has now been found that excellent results are obtained in the alkaline discharge printing processes of German Offenlegungsschriften Nos. 2,836,391 and 2,856,283 if the dischargeable disperse dyestuffs employed are dyestuffs of the formula I

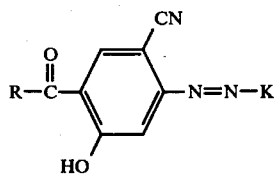

in which R and K have the meanings mentioned later in the text.

The present invention therefore relates to a process for the production of white patterns or patterns of various colours on a coloured substrate on textile materials containing, or consisting of, hydrophobic synthetic fibres, in particular polyester fibres, or on textile materials based on mixed fibres composed of polyester and cellulose, in particular polyester/cotton fibres, by impregnating the materials with dye liquors which, besides the customary dyeing and padding auxiliaries, contain disperse dyestuffs which are dischargeable to white, and, if mixed fibre textiles are processed, contain, if desired, reactive dyestuffs which are dischargeable to white and which have, as a reactive anchor, a group of the formula —SO$_2$—CH$_2$—CH$_2$—Hal,

—SO$_2$—CH$_2$—CH$_2$—O—SO$_3$M,

—NH—SO$_2$—CH$_2$—CH$_2$—O—SO$_3$M and

—SO$_2$—CH=CH$_2$ and printing on, in the desired pattern, a discharge reserve paste which, besides the discharge reserving agent, also contains, if desired, dyestuffs which are resistant to discharging agents, in which connection the sequence of impregnating and printing on the discharge reserve paste is immaterial and it is also possible to replace the impregnation by printing with an appropriate printing paste, and by subsequently subjecting the material to a heat treatment at temperatures of 100° to 230° C., in which process, if no reactive dyestuffs which are dischargeable to white are present, the discharge reserving agent employed is a base which produces a pH value of at least 8 in a 5% strength aqueous solution, or is a discharge reserving agent based on sulphites which contains an alkali metal sulphite or an alkali metal bisulphite in combination with an alkali metal carbonate or bicarbonate and, if appropriate, an aldehyde, and which, if appropriate, contans a nonionic detergent, and if the abovementioned reactive dyestuffs which are dischargeable to white are present, the discharge reserving agent based on sulphites is employed, characterised in that the dischargeable disperse dyestuffs employed are dyestuffs of the formula I

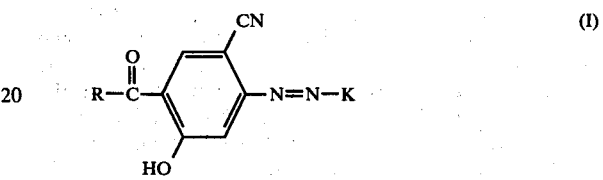

in which R denotes optionally substituted alkyl having 1 to 8, preferably 1 to 4, C atoms, optionally substituted alkoxy having 1 to 8 C atoms, preferably 1 to 4 C atoms, and K denotes the radical of a coupling component of the benzene, naphthalene, pyridine, benzpyridine, diazole, thiazole, indole, carbazole, oxazole or diazine series or the series of enolisable 1,3-dicarbonyl compounds, the molecule of which dyestuffs contains not more than one esterified carboxyl group.

Substituted and unsubstituted alkyl or alkoxy radicals can, as such or when they are present as substituents, be straight-chain or branched. Examples of alkoxy radicals represented by R are methoxy, ethoxy, n-propoxy, i-propoxy, n-butoxy, i-butoxy, sec.-butoxy, n-pentoxy, i-pentoxy, n-hexoxy, i-hexoxy, n-heptoxy, i-heptoxy and i-octoxy.

Examples of alkyl radicals represented by R are: methyl, ethyl, n-propyl, i-propyl, n-butyl, i-butyl, sec.-butyl, t-butyl, n-pentyl, i-pentyl, n-hexyl, i-hexyl, n-heptyl, i-heptyl and i-octyl.

The alkyl and alkoxy radicals represented by R are, independently of one another, optionally monosubstituted or disubstituted by chlorine, bromine, cyano, hydroxyl, alkoxy having 1 to 4 C atoms, alkeneoxy having 3 or 4 C atoms, hydroxyalkoxy having 2 to 4 C atoms, alkoxyalkoxy having a total of 3 to 8 C atoms, alkylcarbonyloxy having 2 to 4 C atoms, optionally substituted benzoyloxy, optionally substituted phenyl and optionally substituted phenoxy. The alkyl or alkoxy groups represented by R can carry an OH group as a third substituent. Unsubstituted or monosubstituted alkyl or alkoxy groups are preferred for R.

The following are examples of substituents on optionally substituted phenyl, phenoxy or benzoyl radicals: alkyl having 1 to 4 C atoms, alkoxy having 1 to 4 C atoms, fluorine, chlorine, bromine and nitro, both monosubstitution and disubstitution being possible; the unsubstituted radicals are preferred, however.

Those meanings of R in which several preferred characteristics are combined, are particularly preferred.

Coupling components KH of the benzene series are aniline derivatives of the formula

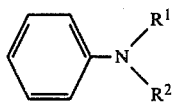

wherein $R^1$ denotes hydrogen, alkyl or alkenyl and $R^2$ denotes alkyl, alkenyl, cycloalkyl, phenyl, alkylcarbonyl, benzoyl, alkylsulphonyl or phenylsulphonyl, and in which the N-alkyl, N-alkenyl, N-cycloalkyl, N-phenyl, N-acyl, N-alkylsulphonyl and N-phenylsulphonyl radical can optionally be substituted and in which the nucleus can optionally be monosubstituted or polysubstituted by optionally substituted alkyl having 1 to 4, preferably 1 or 2, C atoms, optionally substituted alkoxy having 1 to 4, preferably 1 or 2, C atoms, alkeneoxy having 3 or 4 C atoms, optionally substituted phenoxy, optionally substituted phenyl, fluorine, chlorine, bromine, optionally substituted alkylcarbonylamino, optionally substituted benzoylamino, alkenylcarbonylamino, optionally substituted alkylsulphonylamino, optionally substituted phenylsulphonylamino, optionally substituted N-alkyl-N-alkylsulphonylamino or N-alkyl-N-phenylsulphonylamino, optionally substituted alkoxycarbonylamino, alkeneoxycarbonylamino, cycloalkoxycarbonylamino or phenoxycarbonylamino, optionally substituted alkylaminocarbonylamino, alkenylaminocarbonylamino, cycloalkylaminocarbonylamino or phenylaminocarbonylamino or hydroxyl, or are phenols in which the nucleus can be substituted by alkyl having 1 to 4 C atoms or optionally substituted alkylcarbonylamino or benzoylamino.

Coupling components of the naphthalene series are 1-naphthylamines or 2-naphthylamines of the formula

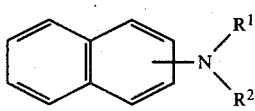

wherein $R^1$ denotes hydrogen, alkyl or alkenyl and $R^2$ denotes alkyl, alkenyl, cycloalkyl, phenyl, alkylcarbonyl, benzoyl, alkylsulphonyl or phenylsulphonyl, such as, for example, N-monoalkyl-, N,N-dialkyl-, N-monoalkenyl-, N,N-dialkenyl-, N-alkyl-N-alkenyl-, N-cycloalkyl, N-monophenyl-, N-phenyl-N-alkyl- or N-phenyl-N-alkenyl-1-naphthylamines or N-monoalkyl-, N,N-dialkyl-, N-monoalkenyl-, N,N-dialkenyl-, N-alkyl-N-alkenyl-, N-cycloalkyl-, N-monophenyl-, N-phenyl-N-alkyl- or N-phenyl-N-alkenyl-2-naphthylamines in which the N-alkyl or N-phenyl radicals can optionally be substituted and in which the nucleus can optionally be substituted by alkyl having 1 to 4 C atoms, alkoxy having 1 to 4 C atoms, chlorine, bromine, aminosulphonyl, N-monoalkyl-substituted aminosulphonyl or N,N-dialkyl-substituted aminosulphonyl, it being possible for the alkyl radicals in turn, independently of one another, to be optionally monosubstituted or polysubstituted, or are 1-naphthols or 2-naphthols in which the nucleus can optionally be substituted by aminocarbonyl, monoalkylaminocarbonyl, dialkylaminocarbonyl or phenylaminocarbonyl which are, independently of one another, optionally substituted, optionally substituted alkoxycarbonyl, alkeneoxycarbonyl, cycloalkoxycarbonyl or phenoxycarbonyl, amino, optionally substituted alkylcarbonylamino, alkenylcarbonylamino, optionally substituted benzoylamino, optionally substituted alkyl-sulphonylamino, optionally substituted phenylsulphonylamino, alkyl having 1 to 4, preferably 1 or 2, C atoms, alkoxy having 1 to 4, preferably 1 or 2, C atoms, chlorine or bromine, aminosulphonyl and monoalkylaminosulphonyl and dialkylaminosulphonyl in which the radicals can independently of one another, optionally be substituted.

Examples of coupling components of the pyridine series are the pyridones of the formula II

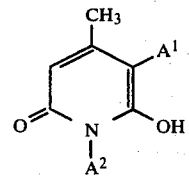

in which $A^1$ denotes cyano, nitro, optionally substituted aminocarbonyl or hydrogen and $A^2$ denotes hydrogen, optionally substituted amino or optionally substituted alkyl having 1 to 8 C atoms, and also the pyridines of the formula III

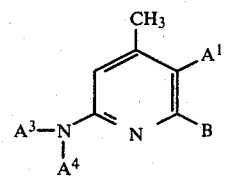

in which $A^3$ and $A^4$ denote hydrogen or, independently of one another, denote optionally substituted alkyl having 1 to 8 C atoms, alkenyl having 3 to 5 C atoms or cycloalkyl having 5 or 6 C atoms and B represents $NA^5A^6$ or optionally substituted alkoxy or alkylthio having 1 to 8 C atoms and $A^5$ and $A^6$ independently of one another denoe hydrogen or optionally substituted alkyl having 1 to 8 C atoms, alkenyl having 3 to 5 C atoms or cycloalkyl having 5 or 6 C atoms and $A^1$ has the meanings mentioned above, or the pyridines of the formula IV

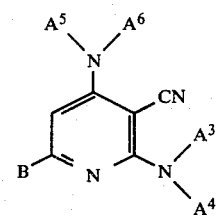

in which $A^3$ to $A^6$ and B have the meanings mentioned above. The following are examples of coupling components of the benzpyridine series: aminoquinolines, N-monoalkylaminoquinolines, N,N-dialkylaminoquinolines, N-monoalkenylaminoquinolines and N,N-dialkenylaminoquinolines which have 1-8 C atoms in the alkyl radicals and 3-5 C atoms in the alkenyl radicals and in which the alkyl or alkenyl radical can optionally be substituted, N-cycloalkylaminoquinolines or N-phenylaminoquinolines, hydroxyquinolines and hydroxyisoquinolines and N-alkylquinolones, N-alkenylquinolones, N-phenylquinolones, N-alkylisoquinolones, N-alkenylisoquinolones and N-phenylisoquinolones in which the alkyl radical has 1-8 C atoms and can optionally be substituted. The following are examples of coupling components of the diazole series: pyrazolones, aminopyrazoles and N-alkylpyrazolones, N-phenylpyrazolones, N-alkylaminopyrazoles and N-phenylaminopyrazoles in which the alkyl radical has 1-8, preferably 1-4, C atoms and in which the alkyl or phenyl radical can optionally be substituted and in which the nucleus can optionally be substituted by optionally substituted alkyl or phenyl or by optionally substituted alkoxycarbonyl.

Coupling components belonging to the series of enolisable 1,3-dicarbonyl compounds are, for example, optionally substituted acetoacetylarylamides, especially acetoacetanilide which is substituted in the nucleus. Suitable substituents are halogen, alkyl, hydroxyl and alkoxy.

The following are examples of coupling components of the thiazole series: 2-aminothiazoles and N-monoalkylaminothiazoles and N,N-dialkylaminothiazoles in which the alkyl radicals have 1-8 C atoms and, independently of one another, are optionally substituted and in which the nucleus can optionally be substituted by optionally substituted alkyl having 1-4 C atoms, alkenyl, cycloalkyl, aralkyl, aryl, hetero-aryl, hydroxyl, amino, alkylcarbonylamino, benzoylamino, alkylsulphonylamino or phenylsulphonylamino.

The following are examples of coupling components of the indole series: indole and N-alkylindole in which the alkyl radical has 1-8 C atoms and can optionally be substituted and in which the nucleus can optionally be substituted by alkyl or alkoxy each of which has 1-4 C atoms, chlorine or bromine.

The following are examples of coupling components of the carbazole series: carbazole and N-alkylcarbazole in which the alkyl radical has 1-8 C atoms and can optionally be substituted and in which the nucleus can optionally be substituted by hydroxyl, alkoxy having 1-4 C atoms, chlorine or bromine.

The following are examples of coupling components of the oxazole series: hydroxyisooxazoles in which the nucleus can optionally be substituted by optionally substituted alkyl or optionally substituted alkoxy each of which has 1-4 C atoms, phenyl, chlorine or bromine.

The following are examples of coupling components of the diazine series: N,N-dialkylbarbituric acids, N,N-diarylbarbituric acids or N-alkyl-N-arylbarbituric acids, having 1-8, preferably 1-4, C atoms in the alkyl radicals.

The following are examples of preferred aniline coupling components which can be N-monoalkyl-substituted, N,N-dialkyl-substituted, N-monoalkenyl-substituted, N,N-dialkenyl-substituted, N-alkyl-N-alkenyl-substituted, N-monocycloalkyl-substituted, N-alkyl-N-cycloalkyl-substituted, N-alkenyl-N-cycloalkyl-substituted, N-phenyl-substituted, N-alkyl-N-phenyl-substituted or N-alkenyl-N-phenyl-substituted, it being possible for the N-alkyl, N-alkenyl, N-cycloalkyl or N-phenyl substituents to be optionally substituted: aniline, 2-chloroaniline, 3-chloroaniline, o-toluidine, m-toluidine, o-anisidine, m-anisidine, 2,5-dimethoxyaniline, 2,5-diethoxyaniline, 2,5-dimethylaniline, 2,5-diethylaniline, 2-methoxy-5-methylaniline, 2-methoxy-5-chloroaniline, 2-ethoxy-5-methylaniline, 2-ethoxy-5-chloroaniline, 3-(optionally substituted) alkylcarbonylaminoaniline, 3-(optionally substituted) arylcarbonylaminoaniline, 3-(optionally substituted) alkylsulphonylaminoaniline, 3-(optionally substituted) arylsulphonylaminoaniline, 3-(optionally substituted) alkoxycarbonylaminoaniline, 3-(optionally substituted) phenoxycarbonylaminoaniline, 3-(optionally substituted) monoalkylaminocarbonylaminoaniline, 3-(optionally substituted) dialkylaminocarbonylaminoaniline, 3-phenylaminocarbonylaminoaniline, 3-N-alkyl-N-phenylaminocarbonylaminoaniline, 2-chloro-5-(optionally substituted) alkylcarbonylaminoaniline, 2-bromo-5-(optionally substituted) alkylcarbonylaminoaniline, 2-($C_1$ to $C_4$)-alkyl-5-(optionally substituted) alkylcarbonylaminoaniline, 2-(optionally substituted) alkoxy-5-(optionally substituted) alkylcarbonylaminoaniline, 2-chloro-5-(optionally substituted) arylcarbonylaminoaniline, 2-bromo-5-(optionally substituted) arylcarbonylaminoaniline, 2-($C_1$ to $C_4$)-alkyl-5-(optionally substituted) arylcarbonylaminoaniline, 2-(optionally substituted) alkoxy-5-(optionally substituted) arylcarbonylaminoaniline, 2-chloro-5-(optionally substituted) alkylsulphonylaminoaniline, 2-bromo-5-(optionally substituted) alkylsulphonylaminoaniline, 2-($C_1$ to $C_4$)-alkyl-5-(optionally substituted) alkylsulphonylaminoaniline, 2-(optionally substituted) alkoxy-5-(optionally substituted) alkylsulphonylaminoaniline, 2-chloro-5-(optionally substituted) arylsulphonylaminoaniline, 2-bromo-5-(optionally substituted) arylsulphonylaminoaniline, 2-($C_1$ to $C_4$)-alkyl-5-(optionally substituted) arylsulphonylamino aniline, 2-(optionally substituted) alkoxy-5-(optionally substituted) arylsulphonylaminoaniline, 2-chloro-5-(optionally substituted) alkoxycarbonylaminoaniline, 2-bromo-5-(optionally substituted) alkoxycarbonylaminoaniline, 2-($C_1$ to $C_4$)-alkyl-5-(optionally substituted) alkoxycarbonylaminoaniline, 2-(optionally substituted) alkoxy-5-(optionally substituted) alkoxycarbonylamino, 2-chloro-5-alkeneoxycarbonylaminoaniline, 2-bromo-5-alkeneoxycarbonylaminoaniline, 2-($C_1$ to $C_4$)-alkyl-5-alkeneoxycarbonylaminoaniline, 2-(optionally substituted) alkoxy-5-alkeneoxycarbonylaminoaniline, 2-chloro-5-cycloalkoxycarbonylaminoaniline, 2-bromo-5-cycloalkoxycarbonylaminoaniline, 2-($C_1$ to $C_4$)-alkyl-5-cycloalkoxycarbonylaminoaniline, 2-(optionally substituted) alkoxy-5-cycloalkoxycarbonylaminoaniline, 2-chloro-5-phenoxycarbonylaminoaniline, 2-bromo-5-phenoxycarbonylaminoaniline, 2-($C_1$ to $C_4$)-alkyl-5-phenoxycarbonylaminoaniline, 2-(optionally substituted) alkoxy-5-phenoxycarbonylaminoaniline, 2-chloro-5-(optionally substituted) monoalkylaminocarbonylaminoaniline, 2-bromo-5-(optionally substituted) monoalkylaminocarbonylaminoaniline, 2-($C_1$ to $C_4$)-alkyl-5-(optionally substituted) monoalkylaminocarbonylaminoaniline, 2-(optionally substituted) alkoxy-5-(optionally substituted) monoalkylaminocarbonylaminoaniline, 2-chloro-5-(optionally substituted) dialkylaminocarbonylaminoaniline, 2-bromo-5-(optionally substituted) dialkylaminocarbonylaminoaniline, 2-($C_1$ to $C_4$)-alkyl-5-(optionally substituted) dialkylaminocarbonylaminoaniline, 2-chloro-5-N-alkyl-N-phenylaminocarbonylaminoaniline, 2-bromo-5-N-alkyl-N-phenylaminocarbonylaminoaniline, 2-($C_1$ to $C_4$)-alkyl-5-N-alkyl-N-phenylaminocarbonylaminoaniline, 2-(optionally substituted) alkoxy-5-N-alkyl-N-phenylaminocarbonylaminoaniline, 2-chloro-5-phenylaminocarbonylaminoaniline, 2-bromo-5-phenylaminocarbonylaminoaniline, 2-($C_1$ to $C_4$)-alkyl-5-phenylaminocarbonylaminoaniline, 2-(optionally substituted) alkoxy-5-phenylaminocarbonylaminoaniline or optionally substituted diphenylamine.

The following are examples of preferred phenyl coupling components: o-, m- or p-cresol or 3-alkylcarbonylaminophenol or 3-arylcarbonylaminophenol in which the alkyl or aryl radical is optionally substituted. The following are examples of preferred naphthylamino coupling components, which can be N-monosubstituted or, independently of one another, N,N-disubstituted by alkyl, alkenyl, cycloalkyl or phenyl, it being possible for the N-alkyl substituents and N-phenyl substituents to be optionally substituted: 1-naphthylamine, 2-, 5- or 7-hydroxy-1-naphthylamine, 2-alkoxy-1-naphthylamine, 2-naphthylamine, 5-, 6-, 7- or 8-hydroxy-2-naphthylamine, 5-aminosulphonyl-2-naphthylamine or 5-monoalkylaminosulphonyl-2-naphthylamine or 5-N,N-dialkylaminosulphonyl-2-naphthylamine in which, independently of one another, the alkyl radical is optionally substituted.

The following are examples of preferred naphthol coupling components: 1-naphthol, 2-naphthol or 6-aminosulphonyl-2-naphthol which can be N-monosubstituted or N,N-disubstituted by alkyl, alkenyl, cycloalkyl or phenyl, independently of one another, and in which the alkyl or phenyl radicals can, independently of one another, be optionally substituted, 3-alkoxycarbonyl-2-naphthol, 3-phenoxycarbonyl-2-naphthol, or 3-aminocarbonyl-2-naphthol, 3-N-monoalkylaminocarbonyl-2-naphthol, 3-N-monoarylaminocarbonyl-2-naphthol, 3-N,N-dialkylaminocarbonyl-2-naphthol or 3-N,N-diarylaminocarbonyl-2-naphthol in which the N-alkyl or N-aryl radical is optionally substituted.

The following are examples of preferred coupling compositions of the pyridine series: 3-cyano-4-methyl-6-hydroxypyrid-2-one or N-alkyl-3-cyano-4-methyl-6-hydroxypyrid-2-one, N-alkenyl-3-cyano-4-methyl-6-hydroxypyrid-2-one, N-cycloalkyl-3-cyano-4-methyl-6-hydroxypyrid-2-one or N-aryl-3-cyano-4-methyl-6-hydroxypyrid-2-one in which the alkyl or aryl radicals are optionally substituted 2,6-diamino-3-cyano-4-methylpyridines, 2,4,6-triamino-3-cyanopyridines, 2-amino-6-alkoxy-3-cyano-4-methylpyridines or 2-amino-6-alkoxy-5-cyano-4-methylpyridines in which the amino groups can be monosubstituted or disubstituted by alkyl groups which are, independently of one another optionally substituted, or by alkenyl, or in which the alkoxy groups can be optionally substituted.

The following are examples of preferred coupling compositions of the benzpyridine series: 8-aminoquinoline in which the amino group can be monosubstituted by optionally substituted alkyl or by alkenyl or cycloalkyl or can be disubstituted by alkyl and/or alkenyl groups which, independently of one another are optionally substituted, or 4-hydroxy-2-quinoline or 3-hydroxy-1-isoquinolone which can optionally be substituted by N-monoalkyl or N-monoalkenyl, it being possible for the alkyl radicals to be optionally substituted.

The following are examples of preferred coupling components of the diazole series: N-alkyl-substituted, N-alkenyl-substituted, N-cycloalkyl-substituted or N-aryl-substituted pyrazol-3-ones in which the N-alkyl or N-aryl radical can be optionally substituted and which can be substituted in the 5-position by optionally substituted alkyl or aminocarbonyl which can be monosubstituted or disubstituted by optionally substituted alkyl or alkenyl, or which can be substituted in the 5-position by optionally substituted alkoxycarbonyl or alkeneoxycarbonyl, or 3-amino-5-alkyl-N-arylprazoles in which the amino group can be monosubstituted by optionally substituted alkyl or by alkenyl or cycloalkyl, or can be disubstituted by alkyl and/or alkenyl groups which, independently of one another, are optionally substituted.

Preferred coupling components of the thiazole series are, for example: 2-aminothiazole in which the amino group can be monosubstituted by optionally substituted alkyl, or by alkenyl or cycloalkyl or can be disubstituted by alkyl and/or alkenyl groups which, independently of one another, are optionally substituted.

The following are examples of preferred coupling compositions of the carbazole series: carbazole, N-alkylcarbazole in which the N-alkyl radical can be optionally substituted, N-alkenylcarbazole or 3-hydroxycarbazole.

Preferred coupling components of the oxazole series are, for example: 5-hydroxyisooxazoles which can be substituted in the 3-position by optionally substituted alkyl or phenyl, optionally substituted alkoxy, chlorine or bromine.

The following are examples of preferred enolisable 1,3-dicarbonyl compounds: acetoacetanilide and its N-chlorophenyl, N-bromophenyl, N-methylphenyl, N-hydroxyphenyl or N-methoxyphenyl homologues.

Optionally substituted alkyl radicals which can be present in the substituents $R^1$, $R^2$ and $A^3$ to $A^6$ of the coupling components mentioned above, are, above all, linear or branched alkyl radicals having 1 to 8 atoms, such as methyl, ethyl, n-propyl, i-propyl, n-butyl, i-butyl, sec.-butyl, n-pentyl, i-pentyl, n-hexyl or i-octyl. Optionally substituted alkylcarbonylamino, alkylsulphonylamino, N-alkyl-N-alkylsulphonylamino, N-alkyl-N-phenylsulphonylamino, alkylaminocarbonylamino or alkoxycarbonylamino groups and also optionally substituted monoalkylaminocarbonyl, dialkylaminocarbonyl, monoalkylaminosulphonyl or dialkylaminosulphonyl groups which can be present as substituents in the nuclei of coupling components K, have 1–8, preferably 1–4, C atoms.

Alkenyl radicals of the coupling components mentioned above are, above all, alkenyl radicals having 3 to 5 C atoms, such as, for example, allyl, methallyl or crotyl. Cycloalkyl radicals of the coupling components mentioned above are, above all, cycloalkyl radicals having 5 or 6 C atoms, that is to say cyclopentyl or cyclohexyl. Alkenyl and cycloalkyl radicals of the coupling components mentioned above are preferably unsubstituted. Optionally substituted aryl radicals of the coupling components mentioned above are, above all, naphthyl and especially phenyl radicals.

The linear or branched alkyl radicals of the coupling components can carry, for example, the following substituents: hydrozyl, alkoxy having 1 to 4 C atoms, alkenyloxy having 3 to 5 C atoms, optionally substituted phenoxy, cycloalkoxy having 5 or 6 C atoms, hydroxyalkoxy, alkylcarbonyloxyalkoxy and phenoxyalkoxy having 2 to 4 C atoms in the alkoxy radical and in the alkylcarbonyl radical, alkoxyalkoxy having 3 to 8 C atoms, hydroxyalkoxyalkoxy, alkylcarbonyloxyalkoxyalkoxy and phenoxyalkoxyalkoxy having 4 to 12 C atoms in the alkoxyalkoxy radical and 2 to 4 C atoms in the alkylcarbonyl radical; alkoxyalkoxyalkoxy having 5 to 16 C atoms; alkylcarbonyloxy which is optionally substituted by hydroxyl, chlorine, bromine, alkoxy having 1 to 4 C atoms or phenoxy and which has 2 to 4 C atoms, and optionally substituted benzoyloxy; alkoxycarbonyloxy which is optionally substituted by hydroxyl, chlorine, bromine, alkoxy having 1 to 4 C atoms, or phenoxy and which has 1 to 4 C atoms in the alkoxy group; alkeneoxycarbonyloxy having 3 to 5 C atoms in the alkeneoxy group; cycloalkoxycarbonyloxy having 5 or 6 C atoms in the cycloalkoxy group; optionally substituted phenoxycarbonyloxy; monoalkylaminocarbonyloxy which is optionally substituted by hydroxyl, chlorine, bromine, alkoxy having 1 to 4 C atoms or phenoxy and which has 1 to 8 C atoms in the alkylamino group; optionally substituted monoarylaminocarbonyloxy; optionally substituted phenyl; chlorine; bromine, and cyano, and, in the event that R is optionally substituted alkyl, they can also have the following substituents:

Alkoxycarbonyl having 1 to 8 C atoms in the alkoxy group, which is optionally substituted; alkeneoxycarbonyl having 3 to 5 C atoms in the alkeneoxy group; cycloalkoxycarbonyl having 5 or 6 C atoms in the cycloalkoxy group; and phenoxycarbonyl in which the phenoxy radical is optionally substituted.

The aryl radicals, in particular the naphthyl or phenyl radicals, can be monosubstituted or disubstituted, particularly by fluorine, chlorine, bromine, trifluoromethyl, alkyl having 1 to 4 C atoms and alkoxy having 1 to 4 C atoms.

Coupling components KH which are particularly preferred are those belonging to the 6-hydroxypyrid-2-one, aminopyridine, 2-naphthol, 1-naphthylamine, 2-aminothiazole, indole or carbazole series, and particularly coupling components belonging to the aniline series. Dyestuffs of the formula I in which R represents optionally substituted alkoxy are also preferred.

Dyestuffs of the formula I which are particularly preferred are those composed of preferred diazo and coupling components and, in particular, those composed of diazo and coupling components which are particularly preferred.

If a textile material containing only hydrophobic fibres, or only the hydrophobic fibre component of a mixed textile, is to coloured, the alkaline discharge printing process is effected in a manner which is in itself known by padding the textile materials with dye liquors or printing them with colour pastes which contain one or more dyestuffs of the formula I as well as the known, customary dyeing auxiliaries, such as, for example, dispersing agents, wetting agents, anti-foaming agents and padding auxiliaries or printing ink thickeners. Padded textile webs are squeezed out to a liquor pick-up of 50 to 120%. After this initial padding or printing process, the goods can be dried or incipiently dried, or can be processed further "wet-on-wet" without any separate drying operation. The textile webs are then printed with a discharge reserve printing paste containing, as the discharging agent, a base which produces a pH value of at least 8 in a 5% strength aqueous solution, and also the known additives, particularly thickeners, which are customary in printing pastes for textile printing.

The operation of padding or printing with a dye liquor or colour paste, respectively, mentioned above as the first process stage and the printing with the discharge reserve printing paste mentioned as the second stage can also be exchanged with one another. In this case, after being printed with the discharge printing paste, the textile material is overpadded with the dye liquor for the ground dyeing or is overprinted with the colour paste. In this sequence too, the process can be carried out "wet-on-wet", or the textile material can be incipiently dried or dried after being printed with the discharge reserve paste. The padded and printed textile webs are then subjected to a heat treatment at a temperature between 100° and 230° C. Within the lower temperature range from about 100° to 110° C., it is preferable to supply the heat by means of superheated steam. Hot air is preferably used as the heat transfer agent for heat treatments which are carried out at temperatures between 160° and 230° C. After the heat treatment, which results in the disperse dyestuffs being fixed and the dyestuffs of the formula I being destroyed on the areas printed with the discharge reserve printing paste, the textiles are subjected to an after-treatment in the manner customary for polyester, are rinsed under hot and cold conditions and are dried. In a particular embodiment of the discharge printing process, the padding liquor additionally contains, as well as dyestuffs of the formula I, dyestuffs which are resistant to alkali and are thus not destroyed by the alkaline discharge reserve printing pastes which are to be employed. Multi-coloured patterns are obtained if the procedure is in other respects as indicated above. As already described above, in a further embodiment of the process the dyestuffs of the formula I are not applied to the whole fabric by padding with a padding liquor, but are printed onto the fabric similarly in the form of printing pastes.

The textile prints are then fixed and finished subsequently as already described above. In this process too, it is possible to add dyestuffs which are resistant to alkali to the colour printing pastes which are printed on. In this case too, multi-colour patterns are obtained.

A further possible means of carrying out the process according to the invention consists in printing discharge reserve printing pastes which, in turn, contain alkali-resistant dyestuffs, onto the ground which has been padded or printed with dyestuffs of the formula I. When the textile materials are subsequently fixed and finished, as described above, multi-coloured patterns are also obtained in this case.

The dyestuffs of the formula I are present in the padding liquors or in the printing pastes in a finely dispersed form such as is customary and known for disperse dyestuffs. The preparation of the padding liquors or printing pastes which are to be employed in accordance with the invention is also effected in a manner which is in itself known by mixing the constituents of the liquor or printing paste with the required quantity of water and liquid, finely dispersed or solid, redispersible formulations of the dyestuffs of the formula I.

Alkali-resistant disperse dyestuffs which can be combined with the dyestuff of the formula I for the production of multi-coloured patterns, are the known commercial dyestuffs belonging to the group comprising azo, azomethine, quinophthalone, nitro or anthraquinone dyestuffs. The following are a few examples of alkali-resistant disperse dyestuffs:

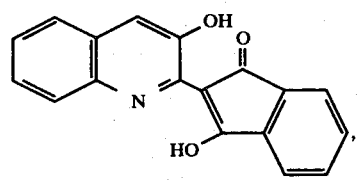

-continued

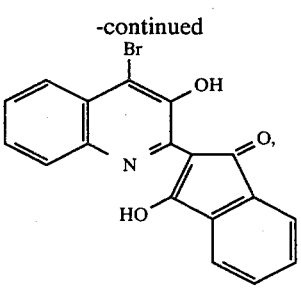

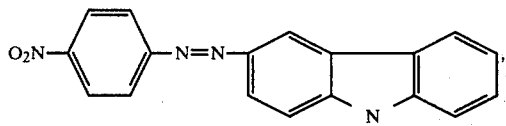

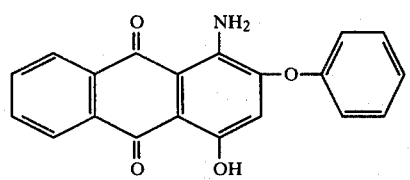

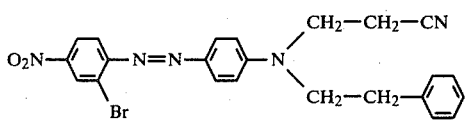

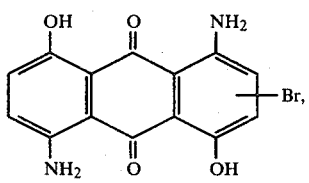

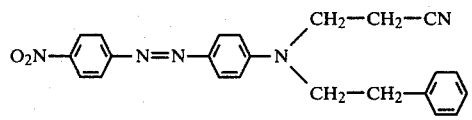

Bases which are present in the discharge reserve printing paste as the discharging agent and which produce a pH value of at least 8 in a 5% strength aqueous solution, are known in large numbers. Examples of such bases are the hydroxides of the alkali and alkaline earth metals, salts of alkaline earth and alkali metals with weak organic or inorganic acids, such as, for example, an alkali metal acetate, alkali metal carbonates or bicarbonates, tri-alkali metal phosphates, ammonia or aliphatic amines, such as, for example, triethylamine, tripropylamine, tributylamine, ethanolamine, dimethylethanolamine, diethylethanolamine, diethanolamine, methyldiethanolamine, ethyldiethanolamine, propyldiethanolamine or triethanolamine. The bases usually employed are alkaline earth metal hydroxides, such as, for example, calcium hydroxide, alkali metal hydroxides, such as, for example, sodium hydroxide or potassium hydroxide, or alkali metal salts of weak inorganic acids, such as, for example, sodium carbonate, trisodium phosphate, sodium silicate or potassium silicate. It is preferable to use, as the base in the discharge reserve printing pastes, sodium hydroxide or potassium hydroxide or, in particular, sodium carbonate or potassium carbonate or sodium bicarbonate or potassium bicarbonate. It is also possible to use mixtures of various bases. The concentration of the base in the discharge reserve printing pastes is advantageously 25 to 250 g/kg, preferably 50 to 130 g/kg. In addition to the said bases, the discharge reserve printing pastes contain the customary additives present in textile printing pastes, in particular thickeners, such as, for example, alginates, starch products, synthetic polymeric thickeners, mineral oils and hydrotropic substances, such as, for example, urea, and also additives which promote wetting, penetration and uptake of dyestuffs. The presence of nonionic detergents, preferably contained in the discharge reserve printing pastes, such as, for example, glycerol and/or polyglycols, such as polyethylene glycol having an average molecular weight of 300 to 400, is particularly advantageous for the discharge process.

The alkaline discharge printing process described makes it possible to apply discharge reserve prints not only to textile materials which consist of hydrophobic fibres, in particular polyester fibres, or which contain a predominant proportion of such fibres, but also to textile materials which contain hydrophobic fibres, in particular polyester fibres, and cellulose fibres in comparable ratios. Polyester/cellulose mixed fabrics of this type can have, for example, a polyester/cellulose ratio by weight of 75:25, 65:35 or 50:50. Discharge reserve prints can be applied to mixed fabrics of this type by the said process in cases where the dye liquor or printing paste, which contains at least one disperse dyestuff of the formula I which is dischargeable to white and, if appropriate, also one or more disperse dyestuffs which are resistant to discharging agents, also contains, in addition, at least one dischargeable reactive dyestuff having a reactive radical of the formula —SO$_2$—CH$_2$—CH$_2$—Hal, or —SO$_2$—CH$_2$—CH$_2$—O—SO$_3$X, or —NH—SO$_2$—CH$_2$—CH$_2$—OSO$_3$X, or

—SO$_2$—CH=CH$_2$ wherein X denotes hydrogen or a metal cation, in particular the sodium cation, and Hal denotes halogen, in particular chlorine or bromine, and, if appropriate, one or more reactive dyestuffs which are resistant to discharging, and where the discharge reserve printing paste, in addition to an alkali metal carbonate or bicarbonate, contans an alkali metal sulphite or bisulphite and, if appropriate, an aldehyde, and where the process is carried out in other respects as already indicated.

The dischargeable reactive dyestuffs to be employed contain one of the fibre-reactive radicals indicated above. It is a common feature of these radicals that they form a vinylsulphonyl group in the presence of alkali by splitting off a sulphate or halide anion. This group which has been formed in the presence of alkali is fixed on cotton or staple rayon, by an addition reaction between an OH group of the cellulose with the vinyl double bond, in the same manner as the vinylsulphonyl radical which is directly attached to the dyestuff radical. Dischargeable reactive dyestuffs containing one of the reactive radicals mentioned above, can belong to all the industrially important groups of dyestuffs. Examples of suitable reactive dyestuffs which are mentioned are the monoazo dyestuffs CI Yellow 13 to 17 and 72 to 74, Orange 7, 15, 16, 23, 24 and 55, Red 21 to 23, 35, 36, 50, 63, 103 to 107 and 112 to 114, Blue 28 and Brown 16;

the disazo dyestuffs CI Blue 76, Blue 98 and Black 5 and 31; the monoazo and/or disazo metal complex dyestuffs CI Violet 4 and 5, Blue 20 and Brown 18; the anthraquinone dyestuffs CI Violet 22 and Blue 19 and 27; and the phthalocyanine dyestuffs CI Blue 21, 38, 77 and 91 and Green 14.

The disperse dyestuffs of the formula I are preent in the padding liquors or in the printing pastes in a finely dispersed form, such as is customary and known for disperse dyestuffs, whereas the reactive dyestuffs are dissolved. The preparation of the padding liquors or printing pastes which are to be employed in accordance with the invention is also effected in a manner which is in itself known by mixing the constituents of the liquors or printing pastes with the required quantity of water and liquid, finely disperse or solid, redispersible formulations of the disperse dyestuffs and solutions or formulations of the reactive dyestuffs.

As in the process of German Offenlegungsschrift No. 3,019,726, it is also advantageous in this case, particularly when coloured discharges are prepared, to replace the additives which, in addition to the said reserving agents, are customary in the reserve pastes, in particular thickeners, such as, for example, aliginates, starch products, synthetic polymeric thickeners, mineral oils or hydrotropic substances, such as, for example, urea, and also additives which promote wetting, penetration and uptake of dyestuffs, or nonionic detergents, such as, for example, glycerol, and/or polyglycols, such as polyethylene glycol having an average molecular weight of 300 to 400, by esters of higher-molecular polyglycols with carboxylic acids.

Polyglycol carboxylic acid esters which can be employed with particular advantage in the reserve pastes to be used in accordance with the invention, are described, for example, in German Auslegeschrift No 1,138,735.

Here too, when preparing the printing paste, it is particularly advantageous to dispense, in accordance with German Offenlegungsschrift No. 2,952,312, with the customary addition of mineral oils and, instead of the latter, to employ printing pastes containing, per kg, 30 to 250 g, preferably 50 to 150 g, of an auxiliary of the general formula VIII $$C_nH_{2n+2-m}[O(CH_2-CH(CH_3)O)_{x/m}-H]_m \quad (VIII)$$

wherein n is an integer from 2 to 6, m is an integer from 1 to 6 and x is a number from 20 to 60, subject to the proviso that m is less than or equal to n, if appropriate in combination with an esterification product formed from higher-molecular polyglycols and higher alkanecarboxylic and alkenecarboxylic acids.

The dyestuffs of the general formula I can be prepared by diazotising a diazo component of the formula V

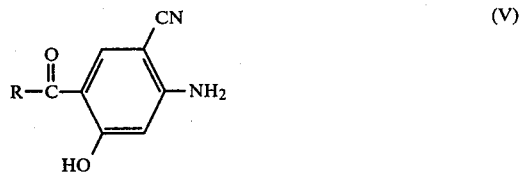

(V)

and coupling the product with a coupling component of the formula VI

K—H  (VI)

The diazotisation of the amine of the formula V is effected in a manner which is in itself known by the action of nitrous acid or compounds which split off nitrous acid. For example, the amines can be dissolved in sulphuric acid, hydrochloric acid or phosphoric acid or in lower aliphatic carboxylic acids, such as, for example, acetic acid or propionic acid, and can be diazotised at 0° to 60° C. by adding nitrosylsulphuric acid or sodium nitrite. The coupling with a coupling component of the general formula VI which contains amino groups on the nucleus is carried out, for example, in an aqueous medium containing hydrochloric or sulphuric acid, in a lower aliphatic carboxylic acid, such as, for example, acetic acid, if appropriate diluted with water, or in a mixture of water and an alcohol which is sparingly soluble in water, such as n-butanol or i-butanol, at temperatures of 0° to 50° C. The temperature range from 0° to 30° C. is preferred in this respect. In order to complete the coupling reaction, it can be advantageous to buffer the pH value of the coupling mixture to a value of 3 to 6, at the start or towards the end of the reaction, by adding bases, such as, for example, sodium acetate.

When coupling with a coupling component of the general formula VI which contains hydroxyl groups on the nucleus, in order to increase the reaction rate, this coupling component is initially taken, together with a base, such as sodium hydroxide or potassium hydroxide solution, sodium carbonate, potassium carbonate or sodium bicarbonate, in an aqueous medium or in a mixture of water and an alcohol which is sparingly soluble in water, and the reaction medium is buffered by adding, for example, sodium acetate. The dyestuffs are isolated in the customary manner by filtration.

The dyestuffs of the general formula I can also be prepared from dyestuffs containing a chlorine or bromine atom in the o-position in relation to the azo bridge, instead of the cyano group present in the diazo component, by replacing the chlorine or bromine by cyano in accordance with replacement processes such as are described, for example, in German Offenlegungsschriften Nos. 1,544,563, 2,310,645, 2,456,495, 2,610,675, 2,724,116, 2,724,117, 2,834,137, 2,834,386, 2,846,438, 2,915,072 and 2,931,081.

The amine of the formula V in which R denotes ethoxy is described in Liebigs Ann. Chem. 1979, 2005 to 2010. It is obtained by a process described in that publication by subjecting a β-oxocarboxylic acid ester to a condensation reaction with ethoxymethylenemalodinitrile in ethanol in the presence of sodium ethylate or by subjecting ethoxymethyleneacetoacetic ester and malodinitrile similarly to a condensation reaction in ethanol in the presence of sodium ethylate, and subsequently acidifying the product. Amines of the formula V in which R is an optionally substituted alkoxy radical as defined above can be prepared analogously if correspondingly substituted β-oxocarboxylic acid esters are used.

Amines of the general formula V in which R is an optionally substituted alkyl radical can be prepared by the working directions in J. Chem. Soc. Perkin I (1979), page 684.

It is possible to prepare by these processes, for example, the diazo components of the general formula V indicated in the following list, which can be employed for the preparation of dyestuffs of the general formula I:

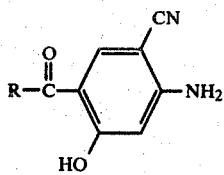

R:
—CH₃; —C₂H₅; —(n)C₃H₇; —(i)C₃H₇; —(n)C₄H₉;
—(i)C₄H₉; —(n)C₅H₁₁; —(i)C₅H₁₁; —(sec.)C₅H₁₁;
—(i)C₇H₁₅; —CH₂CH(C₂H₅)C₄H₉; —CH₂OH;
—CH₂Cl; —CH₂Br; —CH₂—OCH₃; —CH₂—OC₂H₅;

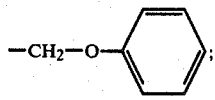

—CH₂—OCH₂—CH=CH₂;

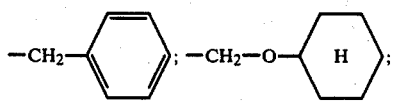

—CH₂—O(i)C₃H₇; —CH₂—O—COCH₃; —CH₂—O—COC₂H₅; —(CH₂)₂OH; —(CH₂)₂Br; —(CH₂)₂—OCH₃;

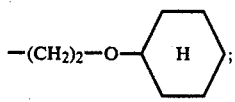

—(CH₂)₂—O(iso)C₃H₇; —CH₂—O(CH₂)₂—OC₂H₅;
—(CH₂)₃—OH; —(CH₂)₃Cl; —(CH₂)₃—OCH₃;
—(CH₂)₃—OC₂H₅; —(CH₂)₃—OC₂H₄—OCH₃;

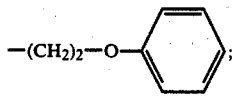

—(CH₂)₂—O—COCH₃; —CH₂CH(OH)CH₂Cl,
—O—C₂H₅; —O—C₂H₅; —O—C₂H₅; —O—CH₃;
—O—C₂H₅; —O—C₂H₅; —O—C₂H₅; —O—CH₃;
—O—CH₃; —O—CH₃; n—C₃H₇—O—; i—C₃H₇—O—; n—C₄H₉—O—; i—C₇H₁₅—O—;
—O—(CH₂)₂OCH₃; —O—C₆H₅; i—C₄H₉—O—;
—O—(CH₂)₂O(CH₂)₂OCH₃; —O—(CH₂)₂OC₆H₅;
—O—CH₂CH(OH)CH₂Cl; —O—CH₂C₆H₅;
—O—(CH₂)₂OCOCH₃; —O—CH₂CH(C₂H₅)C₄H₉;
—O—(CH₂)₂OC₆H₁₁; —O—(CH₂)₂Oi—C₃H₇;
—O—(CH₂)₂OH; —O—(CH₂)₂CN.

As is customary with disperse dyestuffs, the dyestuffs according to the invention are present in as fine as possible a state of distribution in the padding liquors and printing pastes which are employed in the above applications.

The dyestuffs are brought into a fine state of distribution by suspending the dyestuff obtained by manufacture, together with dispersing agents, in a liquid medium, preferably in water, and subjecting the mixture to the action of shearing forces, in the course of which the dyestuff particles initially present are comminuted mechanically to such an extent that an optimum specific surface area is achieved and the sedimentation of the dyestuff is as low as possible. The particle sizes of the dyestuffs are, in general, between 0.5 and 5 μm, preferably about 1 μm.

The dispersing agents used concomitantly in the grinding process can be nonionic or anionic. Examples of nonionic dispersing agents are reaction products of alkylene oxides, such as, for example, ethylene oxide or propylene oxide, with alkylatable compounds, such as, for example, fatty alcohols, fatty amines, fatty acids, phenols, alkylphenols and carboxylic acid amides. Examples of anionic dispersing agents are ligninsulphonates, alkylsulphonates, alkylarylsulphonates or alkylarylpolyglycol ether-sulphates.

The process according to the invention gives discharge prints of high brilliance and having sharp outlines and a satisfactory white ground. It is also possible to produce, by the process according to the invention, coloured prints which are distinguished by exactness of reproduction of detail and purity of colour. The level of fastness of the discharge prints produced in accordance with the invention is excellent, particularly in the case of prints on polyester/cellulos mixed fabrics. The fastness to washing, rubbing, dry cleaning, fixing by dry heat and light should be singled out particularly; in combination with the mechanical strength of the fabrics, which, as a result of the gentle process according to the invention, is not reduced, this fastness substantiates the high use value of the discharge prints produced.

It was particularly surprising that the dyestuffs to be employed in accordance with the invention can be discharged to pure white by such a gentle discharging agent. As is known, the opinion has hitherto been held that this property is only provided in cases where at least two readily saponfiable carboxylic ester groups are present in the dyestuff molecule or where dyestuffs are employed in which the chromophore is attacked by alkali, such as is the case, for example, with the dyestuffs of German Offenlegungsschrift No. 2,836,391.

The illustrative embodiments which follow illustrate the performance of the process according to the invention and the preparation of the dyestuffs employed in the process. % data relate to weight.

EXAMPLE 1

(a) 10 g of the dyestuff of the formula

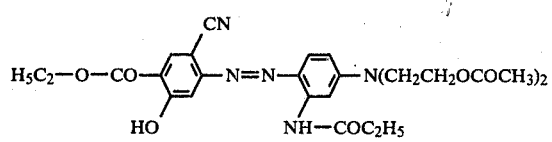

are added, in a finely dispersed form, to a padding liquor containing, per 1,000 parts, 905 parts of water, 5 parts of citric acid and 60 parts of a polymerisation product based on acrylic acid, as an anti-migration agent. This padding liquor is used to pad a polyester fabric based on polyethylene glycol terephthalate at 20° to 30° C. at a sufficient pressure to give a liquor pick-up of approximately 80%. The padded fabric is carefully dried at 60° to 80° C. After drying, it is overprinted with a printing paste containing, per 1,000 parts, 500 parts of a 10% strength aqueous locust bean flour ether thickener, 260 parts of water, 80 parts of calcined sodium carbonate, 80 parts of polyethylene glycol 400 and 80 parts of glycerol. Fixing by means of superheated steam for 7 minutes at 175° C., reductive after-treatment with a 0.2% strength sodium dithionite solution for 15 minutes at 70° to 80° C., soaping and subsequent rinsing and drying gives a red print which has very good fastness properties, above all good fastness to light, fixing by dry heat, rubbing and washing. A very good white ground having sharp outlines is obtained on the areas on which the printing paste containing sodium carbonate is printed.

(b) The dyestuff employed in section (a) is prepared as follows: 20.6 g of the amine of the formula

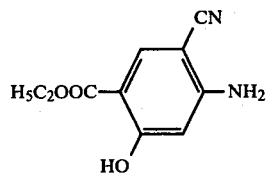

in 125 ml of glacial acetic acid are diazotised at 15° to 20° C. with 34.2 g of 40.5% strength nitrosylsulphuric acid and the product is coupled at 0°–5° C. with a solution of 35.3 g of the amine of the formula

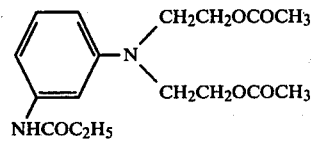

in 450 ml of 50% strength acetic acid, in the presence of 1 g of sulphamic acid. Stirring is continued for 1 hour at this temperature and the dyestuff is precipitated by adding 500 ml of ice water slowly and is filtered off, washed with water and dried under reduced pressure. This gives 50.5 g of a dyestuff of the formula indicated above, of melting point 153°–155° C., which dissolves in o-dichlorobenzene, giving a red colour.

EXAMPLE 2

A 65:35 mercerised polyester/cotton mixed fabric is padded with a mixture consisting of 100 parts by weight of a 10% strength liquid formulation of the dyestuff of the formula indicated in Example 1, section (a), 40 parts by weight of the liquid commercial form of C.I. Reactive Orange 16, 808 parts of cold water, 10 parts by weight of sodium m-nitrobenzenesulphonate, 20 parts by weight of an anti-migration agent based on polyacrylic acid, 2 parts by weight of monosodium phosphate and 20 parts by weight of sodium formate.

The fabric is dried carefully in a hot flue at 80°–100° C. and is overprinted by the screen printing process with a printing paste consisting of 25 parts by weight of the commercial form of [5-(3,6-dichloropyridazin-4-ylcarbonylamino)-2-methyl-3-sulphophenyl]-3-carboxy-4-(2-sulphophenylazo)-5-pyrazol-5-one, 40 parts by weight of the liquid commercial form of C.I. Disperse Yellow 63, 150 parts by weight of urea, 199 parts by weight of cold water, 10 parts by weight of sodium m-nitrobenzenesulphonate, 500 parts by weight of a stock thickener composed of 230 parts by weight of a 4% strength aqueous alginate thickener, 80 parts by weight of a 10% strength aqueous starch ether thickener, 85 parts by weight of water, 25 parts by weight of a 10% strength aqueous solution of the condensation product formed from polyglycol 2000 and stearic acid, and 80 parts by weight of heavy gasoline, 40 parts by weight of sodium bicarbonate, 30 parts by weight of 38° Bé sodium bisulphite solution and 6 parts by weight of 40% strength glyoxal solution.

After being dried, the fabric is fixed with superheated steam for 7 minutes at 175° C. and is subjected to after-treatment as indicated in Example 1.

The dyestuffs of the preparation example which follows and of the subsequent table can also be employed in accordance with the invention, analogously to the instructions in Examples 1 and 2.

EXAMPLE 3

20.6 g of amine are diazotised as in Example 1 and the product is coupled at 0°–10° C. for approximately half an hour with a solution of 29.2 g of the amine of the formula

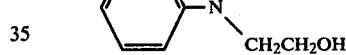

in 700 ml of 75% strength acetic acid, in the presence of 66 g of anhydrous sodium acetate. The mixture is stirred for approximately 3 hours more, while warming to room temperature, and the dyestuff which has been precipitated is then filtered off with suction, washed with water and dried under reduced pressure. This gives 17.5 g of the dyestuff of the formula

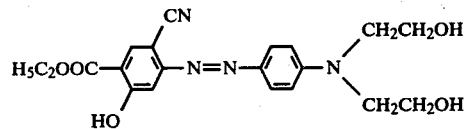

of melting point 127°–129° C., which dissolves in o-dichlorobenzene, giving an orange colour.

TABLE 1

Dyestuffs of the formula

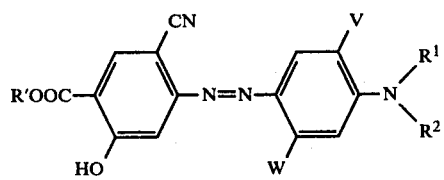

| R' | V | W | R¹ | R² | Shade on polyester |
|---|---|---|---|---|---|
| C₂H₅ | H | H | (CH₂)₂OCOCH₃ | (CH₂)₂CN | orange |
| C₂H₅ | H | H | (CH₂)₂C₆H₅ | (CH₂)₂CN | orange |

TABLE 1-continued

Dyestuffs of the formula

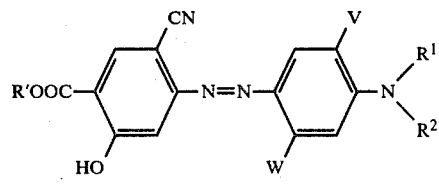

| R' | V | W | $R^1$ | $R^2$ | Shade on polyester |
|---|---|---|---|---|---|
| $C_2H_5$ | H | H | $C_2H_5$ | $(CH_2)_2OH$ | orange |
| $CH_3$ | H | H | $C_2H_5$ | $(CH_2)_2OCOCH_3$ | orange |
| $C_2H_5$ | H | H | $(CH_2)_2OH$ | $(CH_2)_2CN$ | orange |
| $CH_3$ | H | H | $CH(CH_3)_2CN$ | H | orange |
| $n-C_3H_7$ | H | H | $CH(C_2H_5)_2$ | H | orange |
| $n-C_4H_9$ | H | H | $(CH_2)_2OCOOCH_3$ | $CH_2CH=CH_3$ | orange |
| $(CH_2)_2OCH_3$ | H | H | $CH_3O(CH_2)_2$ | $CH_3O(CH_2)_2$ | orange |
| $C_2H_5$ | Cl | H | $(CH_2)_2CN'$ | H | orange |
| $CH_3$ | Cl | H | $(CH_2)_2O(CH_2)_2OCH_3$ | H | orange |
| $C_2H_5$ | $CH_3$ | H | $CH(CH_3)_2$ | H | orange |
| $C_6H_5$ | $CH_3$ | H | $(CH_2)_2OC_6H_5$ | H | orange |
| $C_2H_5$ | H | $CH_3$ | $C_2H_5$ | $C_2H_5$ | orange |
| $(CH_2)_2OC_6H_5$ | H | $CH_3$ | $(CH_2)_2OCOCH_3$ | $(CH_2)_2OCOCH_3$ | orange |
| $CH_3$ | H | $CH_3$ | $(CH_2)_2CN$ | $n-C_3H_7$ | orange |
| $i-C_3H_7$ | H | $CH_3$ | $(CH_2)_2CN$ | $(CH_2)_2OH$ | orange |
| $C_2H_5$ | H | $CH_3$ | $n-C_4H_9$ | $(CH_2)_2CN$ | orange |
| $C_2H_5$ | H | $CH_3$ | $COCH_2OCH_3$ | H | golden yellow |
| $(CH_2)_2O(CH_2)_2OC_2H_5$ | H | $CH_3$ | $(CH_2)_2Cl$ | $(CH_2)_2Cl$ | orange |
| $CH_3$ | H | $CH_3$ | $(CH_2)_2CN$ | $(CH_2)_2OCOC_2H_5$ | orange |
| $(CH_2)_2CN$ | H | H | $C_6H_5$ | H | orange |
| $C_2H_5$ | $OCH_3$ | H | $(CH_2)_2OCOC_3H_7$ | $(CH_2)_2OCOC_3H_7$ | orange |
| $CH_3$ | $OCH_3$ | H | $CH(CH_3)$ | H | orange |
| $(CH_2)_2OH$ | H | $OCH_3$ | $n-C_3H_7$ | $n-C_3H_7$ | orange |
| $C_2H_5$ | $OCH_3$ | $OCH_3$ | $C_2H_5$ | $C_2H_5$ | scarlet |
| $C_2H_5$ | $OCH_3$ | $OCH_3$ | $CH_2CH(OH)CH_2OC_6H_5$ | H | scarlet |
| $CH_3$ | $OCH_3$ | $CH_3$ | $n-C_4H_9$ | $n-C_4H_9$ | scarlet |
| $CH_3$ | $CH_3$ | $CH_3$ | $(CH_2)_2CN$ | $(CH_2)_2OH$ | scarlet |
| $i-C_4H_9$ | $OCH_3$ | Cl | $(CH_2)_2C_6H_5$ | $(CH_2)_2CN$ | scarlet |
| $C_2H_5$ | $CH_3$ | $CH_3$ | $(CH_2)_2OH$ | $(CH_2)_2OH$ | scarlet |
| $(i)C_3H_7$ | $OCH_3$ | $CH_3$ | $CH(CH_3)C_2H_5$ | $(CH_2)_2OH$ | scarlet |
| $CH_3$ | $CH_3$ | Cl | $CH(CH_2OH)C_6H_5$ | H | red |
| $i-C_3H_7$ | H | $NHCOCH_3$ | $C_2H_5$ | $(CH_2)_2CN$ | red |
| $C_2H_5$ | H | $NHCOCH_3$ | $(CH_2)_2CN$ | $CH_2CH=CH_2$ | red |
| $(CH_2)_2OC_6H_5$ | H | $NHCOCH_3$ | $(CH_2)_2CN$ | $(CH_2)_2OH$ | red |
| $CH_3$ | H | $NHCOC_2H_5$ | $C_2H_5$ | $C_2H_5$ | red |
| $CH_3$ | H | $NHCOC_2H_5$ | $(CH_2)_2CN$ | $(CH_2)_2OCOCH_3$ | red |
| $C_2H_5$ | H | $NHCOC_2H_5$ | $[(CH_2)_2O]_2H$ | $[(CH_2)_2O]_2H$ | red |
| $C_2H_5$ | H | $NHCOC_2H_5$ | $CH_2CH(OH)CH_2Cl$ | $CH_2CH(OH)CH_2Cl$ | orange |
| $(i)C_3H_7$ | H | $NHCO-C_4H_{9(n)}$ | $C_2H_5$ | $C_2H_5$ | orange |
| $C_2H_5$ | H | $NHCOC_6H_5$ | $CH_2C_6H_5$ | H | scarlet |
| $[(CH_2)_2O]_2CH_3$ | H | $NHSO_2CH_3$ | $(CH_2)_2OH$ | $(CH_2)_2OH$ | red |
| $C_2H_5$ | Cl | $NHCOCH_3$ | $CH(C_2H_5)_2$ | H | red |
| $C_2H_5$ | Cl | $NHCOCH_3$ | $CH_2CH=CH_2$ | $CH_2CH=CH_2$ | red |
| $CH_3$ | $CH_3$ | $NHCOCH_3$ | $(CH_2)_2CN$ | H | red |
| $C_2H_5$ | $CH_3$ | $NHCOCH_3$ | $(CH_2)_2CN$ | $CH_2CH=CH_2$ | ruby |
| $n-C_4H_9O(CH_2)_2$ | $CH_3$ | $NHCOCH_2OCH_3$ | $C_2H_5$ | $C_2H_5$ | ruby |
| $i-C_3H_7$ | $OCH_3$ | $NHCOCH_3$ | $(CH_2)_2OCOCH_3$ | $(CH_2)_2OCOCH_3$ | violet |
| $CH_3$ | $OCH_3$ | $NHCOCH_3$ | $(CH_2)_2CN$ | $CH_2CH=CH_2$ | violet |
| $C_2H_5$ | $OC_2H_5$ | $NHCOCH_3$ | $(CH_2)_2OH$ | $(CH_2)_2OH$ | violet |
| $C_2H_5$ | $OC_2H_5$ | $NHCOCH_3$ | $(CH_2)_2OCOCH_3$ | $(CH_2)_2OCOCH_3$ | violet |
| $CH_3$ | $O(CH_2)_2OCH_3$ | $NHCOC_2H_5$ | $C_2H_5$ | H | violet |
| $CH_3$ | $O(CH_2)_2OH$ | $NHCOCH_3$ | $CH(CH_3)C_2H_5$ | H | violet |
| (sec.)$C_4H_9$ | H | H | $C_2H_5$ | $C_2H_5$ | scarlet |
| $C_2H_5$ | H | H | $(CH_2)_2OH$ | $(CH_2)_2OH$ | scarlet |
| $CH_3$ | H | H | $(CH_2)_2CN$ | $C_2H_5$ | orange |
| $CH_2-CH=CH_2$ | H | H | $C_6H_5$ | H | orange |
| $CH_3$ | H | H | $(CH_2)_2OCOCH_3$ | $C_2H_5$ | orange |
| $C_2H_5$ | H | H | $(CH_2)_2CN$ | $(CH_2)_2CN$ | golden yellow |
| $(i)C_3H_7$ | H | H | $(CH_2)_2OH$ | $(CH_2)_2OH$ | orange |
| ⟨H⟩ | H | H | $CH_2C_6H_5$ | $CH_3$ | scarlet |
| $(i)C_7H_{15}$ | H | $CH_3$ | $(CH_2)_2OH$ | $(CH_2)_2OH$ | red |
| $CH_3$ | H | $CH_3$ | $(CH_2)_2OCOCH_3$ | $(CH_2)_2OCOCH_3$ | scarlet |
| $CH_3$ | H | $CH_3$ | $(CH_2)_2CN$ | $(CH_2)_2CN$ | orange |
| $C_2H_5$ | H | $CH_3$ | $CH_2C_6H_5$ | $C_2H_5$ | scarlet |

TABLE II

Dyestuffs of the formula

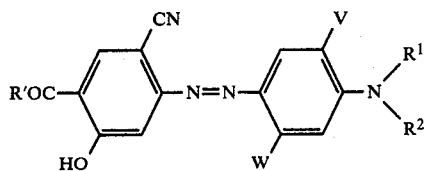

| R' | V | W | R¹ | R² | Shade on polyester |
|---|---|---|---|---|---|
| $CH_3$ | H | H | $(CH_2)_2OCOCH_3$ | $(CH_2)_2CN$ | orange |
| $CH_3$ | H | H | $(CH_2)_2C_6H_5$ | $(CH_2)_2CN$ | orange |
| $C_2H_5$ | H | H | $C_2H_5$ | $(CH_2)_2OH$ | orange |
| $CH_3$ | H | H | $C_2H_5$ | $(CH_2)_2OCOCH_3$ | orange |
| $C_2H_5$ | H | H | $(CH_2)_2OH$ | $(CH_2)_2CN$ | orange |
| $CH_3$ | H | H | $CH(CH_3)_2COOC_4H_9$ | H | orange |
| $n\text{-}C_3\text{—}H_7$ | H | H | $CH(C_2H_5)_2$ | H | orange |
| $n\text{-}C_4H_9$ | H | H | $(CH_2)_2COOCH_3$ | $CH_2CH=CH_3$ | orange |
| $(CH_2)_2OCH_3$ | H | H | $CH_3O(CH_2)_2$ | $CH_3O(CH_2)_2$ | orange |
| $C_2H_5$ | Cl | H | $(CH_2)_2CN$ | H | orange |
| $CH_2\text{—}OCH_3$ | Cl | H | $(CH_2)_2O(CH_2)_2OCH_3$ | H | orange |
| $CH_3$ | $CH_3$ | H | $CH(CH_3)_2$ | H | orange |
| $C_6H_5$ | $CH_3$ | H | $(CH_2)_2OC_6H_5$ | H | orange |
| $C_2H_5$ | H | $CH_3$ | $C_2H_5$ | $C_2H_5$ | orange |
| $CH_2\text{—}OC_6H_5$ | H | $CH_3$ | $(CH_2)_2OCOCH_3$ | $(CH_2)_2OCOCH_3$ | orange |
| $CH_3$ | H | $CH_3$ | $(CH_2)_2CN$ | $n\text{-}C_3H_7$ | orange |
| $i\text{-}C_3H_7$ | H | $CH_3$ | $(CH_2)_2CN$ | $(CH_2)_2OH$ | orange |
| $C_2H_5$ | H | $CH_3$ | $n\text{-}C_4H_9$ | $(CH_2)_2$ | orange |
| $CH_3$ | H | $CH_3$ | $COCH_2OCH_3$ | H | golden yellow |
| $(CH_2)_2O(CH_2)_2OC_2H_5$ | H | $CH_3$ | $(CH_2)_2Cl$ | $(CH_2)_2Cl$ | orange |
| $CH_3$ | H | $CH_3$ | $(CH_2)_2CN$ | $(CH_2)_2OCOC_2H_5$ | orange |
| $(CH_2)_2CN$ | H | H | $C_6H_5$ | H | orange |
| $C_2H_5$ | $OCH_3$ | H | $(CH_2)_2OCOC_3H_7$ | $(CH_2)_2OCOC_3H_7$ | orange |
| $CH_3$ | $OCH_3$ | H | $CH(CH_3)_2COO(CH_2)_2OCH_3$ | H | orange |
| $(CH_2)_2OH$ | H | $OCH_3$ | $n\text{-}C_3H_7$ | $n\text{-}C_3H_7$ | orange |
| $CH_3$ | $OCH_3$ | $OCH_3$ | $C_2H_5$ | $C_2H_5$ | scarlet |
| $C_2H_5$ | $OCH_3$ | $OCH_3$ | $CH_2CH(OH)CH_2OC_6H_5$ | H | scarlet |
| $CH_3$ | $OCH_3$ | $CH_3$ | $n\text{-}C_4H_9$ | $n\text{-}C_4H_9$ | scarlet |
| $C_2H_5$ | H | $NHCOC_2H_5$ | $CH_2CH(OH)CH_2Cl$ | $CH_2CH(OH)CH_2Cl$ | orange |
| $(i)C_3H_7$ | H | $NHCO\text{—}C_4H_{9(n)}$ | $C_2H_5$ | $C_2H_5$ | orange |
| $CH_3$ | H | $NHCOC_6H_5$ | $CH_2C_6H_5$ | H | scarlet |
| $[(CH_2)_2O]_2CH_3$ | H | $NHSO_2CH_3$ | $(CH_2)_2OH$ | $(CH_2)_2OH$ | red |
| $C_2H_5$ | Cl | $NHCOCH_3$ | $CH(C_2H_5)_2$ | H | red |
| $C_2H_5$ | Cl | $NHCOCH_3$ | $CH_2CH=CH_2$ | $CH_2CH=CH_2$ | red |
| $CH_3$ | $CH_3$ | $NHCOCH_3$ | $(CH_2)_2COOCH_3$ | H | red |
| $C_2H_5$ | $CH_3$ | $NHCOCH_3$ | $(CH_2)_2CN$ | $CH_2CH=CH_2$ | red |
| $n\text{-}C_4H_9O(CH_2)_2$ | $CH_3$ | $NHCOCH_2OCH_3$ | $C_2H_5$ | $C_2H_5$ | ruby |
| $i\text{-}C_3H_7$ | $OCH_3$ | $NHCOCH_3$ | $(CH_2)_2OCOCH_3$ | $(CH_2)_2OCOCH_3$ | violet |
| $CH_3$ | $OCH_3$ | $NHCOCH_3$ | $(CH_2)_2CN$ | $CH_2CH=CH_2$ | violet |
| $C_2H_5$ | $OC_2H_5$ | $NHCOCH_3$ | $(CH_2)_2OH$ | $(CH_2)_2OH$ | violet |
| $C_2H_5$ | $OC_2H_5$ | $NHCOCH_3$ | $(CH_2)_2OCOCH_3$ | $(CH_2)_2OCOCH_3$ | violet |
| $CH_3$ | $O(CH_2)_2OCH_3$ | $NHCOC_2H_5$ | $C_2H_5$ | H | violet |
| $CH_3$ | $CH_3$ | $CH_3$ | $(CH_2)_2COOC_2H_5$ | $(CH_2)_2OH$ | scarlet |
| $i\text{-}C_4H_9$ | $OCH_3$ | Cl | $(CH_2)_2C_6H_5$ | $(CH_2)_2CN$ | scarlet |
| $C_2H_5$ | $CH_3$ | $CH_3$ | $(CH_2)_2OH$ | $(CH_2)_2OH$ | scarlet |
| $(i)C_3H_7$ | $OCH_3$ | $CH_3$ | $CH(CH_3)C_2H_5$ | $(CH_2)_2OH$ | orange |
| $CH_3$ | $CH_3$ | Cl | $CH(CH_2OH)C_6H_5$ | H | red |
| $i\text{-}C_3H_7$ | H | $NHCOCH_3$ | $C_2H_5$ | $(CH_2)_2CN$ | red |
| $C_2H_5$ | H | $NHCOCH_3$ | $(CH_2)_2CN$ | $CH_2CH=CH_2$ | red |
| $(CH_2)_2OC_6H_5$ | H | $NHCOCH_3$ | $(CH_2)_2CN$ | $(CH_2)_2OH$ | red |
| $CH_3$ | H | $NHCOC_2H_5$ | $C_2H_5$ | $C_2H_5$ | red |
| $(i)C_3H_7$ | H | $NHCOC_2H_5$ | $(CH_2)_2CN$ | $(CH_2)_2OCOCH_3$ | red |
| $C_2H_5$ | H | $NHCOC_2H_5$ | $[(CH_2)_2O]_2H$ | $[(CH_2)_2O]_2H$ | red |
| $CH_3$ | $O(CH_2)_2OH$ | $NHCOCH_3$ | $CH(CH_3)C_2H_5$ | H | violet |
| $(sec.)C_4H_9$ | H | H | $C_2H_5$ | $C_2H_5$ | scarlet |
| $C_2H_5$ | H | H | $(CH_2)_2OH$ | $(CH_2)_2OH$ | scarlet |
| $CH_3$ | H | H | $(CH_2)_2CN$ | $C_2H_5$ | orange |
| $CH_2\text{—}CH=CH_2$ | H | H | $C_6H_5$ | H | orange |
| $CH_3$ | H | H | $(CH_2)_2OCOCH_3$ | $C_2H_5$ | orange |
| $C_2H_5$ | H | H | $(CH_2)_2CN$ | $(CH_2)_2CN$ | golden yellow |
| $(i)C_3H_7$ | H | H | $(CH_2)_2COOC_2H_5$ | $(CH_2)_2OH$ | orange |
| ⬡H | H | H | $CH_2C_6H_5$ | $CH_3$ | scarlet |
| $(i)C_7H_{15}$ | H | $CH_3$ | $(CH_2)_2OH$ | $(CH_2)_2OH$ | red |
| $CH_3$ | H | $CH_3$ | $(CH_2)_2OCOCH_3$ | $(CH_2)_2OCOCH_3$ | scarlet |

TABLE II-continued

Dyestuffs of the formula

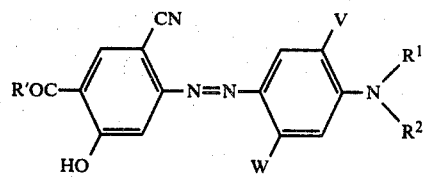

| R' | V | W | R[1] | R[2] | Shade on polyester |
|---|---|---|---|---|---|
| $CH_3$ | H | $CH_3$ | $(CH_2)_2CN$ | $(CH_2)_2CN$ | orange |
| $C_2H_5$ | H | $CH_3$ | $CH_2C_6H_5$ | $C_2H_5$ | scarlet |

TABLE III

Dyestuffs of the formula

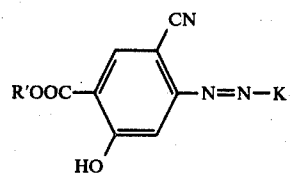

| R' | K | Shade on polyester |
|---|---|---|
| $C_2H_5$ | 4-Hydroxyphen-1-yl | golden yellow |
| $C_2H_5$ | 4-Hydroxy-3-methylphen-1-yl | golden yellow |
| $C_2H_5$ | 4-N—Phenylaminonaphth-1-yl | red |
| $CH_3$ | 4-N—(2-Methoxycarbonylethylamino)-naphth-1-yl | red |
| $C_2H_5$ | 2-Hydroxynaphth-1-yl | red |
| $H_5C_2O(CH_2)_3$ | 2-Hydroxy-6-N—(2-hydroxyethyl)-N—methylamino-sulphonylnaphth-1-yl | red |
| n-$C_3H_7$ | 2,4-Dihydroxyquinolin-3-yl | yellow |
| $C_2H_5$ | 3-Hydroxy-5-methyl-N—phenylpyrazol-4-yl | yellow |
| $C_2H_5$ | 3-Amino-5-methyl-N—phenylpyrazol-4-yl | orange |
| $C_2H_5$ | 2-N—Ethyl-N—(2-hydroxyethyl)-aminothiazol-5-yl | red |
| $CH_3$ | 2-N—(2-Cyanoethyl)-N—(1-acetoethyl)-aminothiazol-5-yl | scarlet |
| $C_2H_5$ | Carbazol-3-yl | orange |
| $C_2H_5$ | N—Ethylcarbazol-3-yl | orange |
| $CH_3$ | N—2-Hydroxyethylcarbazol-3-yl | scarlet |

TABLE IV

Dyestuffs of the formula

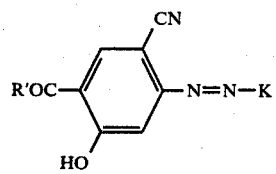

| R' | K | Shade on polyester |
|---|---|---|
| $CH_3$ | 4-Hydroxyphen-1-yl | golden yellow |
| (i)$C_3H_7$ | 4-N—(2-Acetoxyethylamino)-naphth-1-yl | red |
| $C_2H_5$ | 2-Hydroxynaphth-1-yl | red |
| $CH_3$ | 2-Hydroxy-6-N—(2-hydroxyethyl)-N—methylamino-sulphonylnaphth-2-yl | red |
| $CH_3$ | 3-Hydroxy-5-methyl-N—phenylpyrazol-4-yl | yellow |
| $C_2H_5$ | 2-N—Ethyl-N—(2-hydroxyethyl)-aminothiazol-5-yl | red |
| $CH_3$ | 2-N—(2-Cyanoethyl)-N—(2-acetoxethyl)-aminothiazol-5-yl | scarlet |
| (n)$C_3H_7$ | Carbazol-3-yl | orange |
| $C_2H_5$ | N—Ethylcarbazol-3-yl | orange |

TABLE V

Dyestuffs of the formula

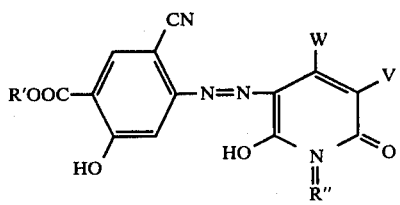

| R' | R'' | V | W | Shade on polyester |
|---|---|---|---|---|
| $C_2H_5$ | H | CN | $CH_3$ | yellow |
| (i)$C_3H_7$ | H | CN | $CH_3$ | yellow |
| $C_2H_5$ | H | $CONH_2$ | $CH_3$ | yellow |
| (i)$C_8H_{17}$ | H | CN | $C_6H_5$ | yellow |
| (n)$C_5H_{11}$ | $CH_3$ | CN | $CH_3$ | yellow |
| H | $CH_3$ | CN | $CH_3$ | yellow |
| $CH_3O(CH_2)_2$ | $C_2H_5$ | CN | $CH_3$ | yellow |
| $CH_3$ | $C_2H_5$ | $NO_2$ | $CH_3$ | yellow |
| n-$C_4H_9$ | n-$C_4H_9$ | CN | $CH_3$ | yellow |
| $C_2H_5$ | n-$C_8H_{17}$ | CN | $CH_3$ | yellow |

TABLE VII

Dyestuffs of the formula

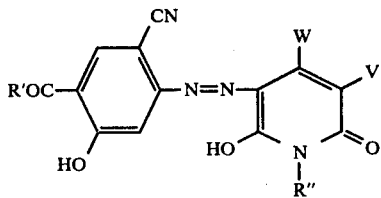

| R' | R'' | V | W | Shade on polyester |
|---|---|---|---|---|
| $CH_3$ | H | CN | $CH_3$ | yellow |
| (i)$C_3H_7$ | H | CN | $CH_3$ | yellow |
| $C_2H_5$ | H | $CONH_2$ | $CH_3$ | yellow |
| (i)$C_8H_{17}$ | H | CN | $C_6H_5$ | yellow |
| (n)$C_5H_{11}$ | $CH_3$ | CN | $CH_3$ | yellow |
| $CH_3O(CH_2)_2$ | $C_2H_5$ | CN | $CH_3$ | yellow |
| $CH_3$ | $C_2H_5$ | $NO_2$ | $CH_3$ | yellow |
| n-$C_4H_9$ | n-$C_4H_9$ | CN | $CH_3$ | yellow |
| $C_2H_5$ | n-$C_8H_{17}$ | CN | $CH_3$ | yellow |

TABLE VIII

Dyestuffs of the formula

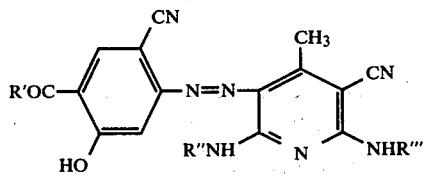

| R' | R'' | R''' | Shade on polyester |
|---|---|---|---|
| $CH_3$ | $CH_3O(CH_2)_3$ | $CH_3O(CH_2)_3$ | scarlet |
| $CH_2$—$OCH_3$ | H | $(CH_2)_3O(CH_2)_2OC_6H_5$ | scarlet |
| $C_2H_5$ | H | $(CH_2)_3O(CH_2)_4OH$ | scarlet |
| $CH_2$—$O(CH_2)_2$—$OCH_3$ | H | $(CH_2)_3O(CH_2)_4OH$ | red |
| $C_2H_5$ | H | $(CH_2)_3O(CH_2)_4OH$ | violet |
| (n)$C_4H_9$ | $CH_3O(CH_2)_3$ | $CH_3O(CH_2)_3$ | scarlet |

What is claimed is:

1. In the process for the preparation of white patterns or patterns of various colors on a colored substrate on textile materials comprising hydrophobic synthetic fibres or on textile materials based on mixed fibres composed of polyester and cellulose comprising impregnating the materials with dye liquores which, besides the customary dyeing and padding auxiliaries, contain disperse dyestuffs which are dischargeable to white, and if mixed fibre textiles are processed, contain, optionally,

TABLE VI

Dyestuffs of the formula

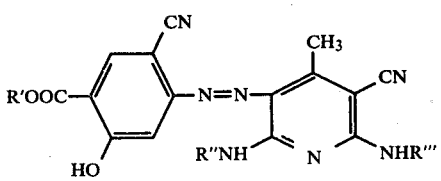

| R' | R'' | R''' | Shade on polyester |
|---|---|---|---|
| $CH_3$ | $CH_3O(CH_2)_3$ | $CH_3O(CH_2)_3$ | scarlet |
| $CH_2$—$OCH_3$ | H | $(CH_2)_3O(CH_2)_2OC_6H_5$ | scarlet |
| $C_2H_5$ | H | $(CH_2)_3O(CH_2)_4OH$ | scarlet |
| $CH_2$—$O(CH_2)_2$—$OCH_3$ | H | $(CH_2)_3O(CH_2)_4OH$ | red |
| $C_2H_5$ | H | $(CH_2)_3O(CH_2)_4OH$ | violet |
| (n)$C_4H_9$ | $CH_3O(CH_2)_3$ | $CH_3O(CH_2)_3$ | scarlet | reactive dyestuffs which are dischargeable to white and which have, as a reactive anchor, a group of the formula —SO₂—CH₂—CH₂—Hal,

—SO₂—CH₂—CH₂—O—SO₃M,

—NH—SO₂—CH₂—CH₂—O—SO₃M and

—SO₂—CH=CH₂ and printing on, in the desired pattern, a discharge reserve paste which, besides the discharge reserving agent, also contains, optionally, dyestuffs which are resistant to discharging agents, and by subsequently subjecting the material to a heat treatment at temperatures of 100° to 230° C., in which process, if no reactive dyestuffs which are dischargeable to white are present, the discharge reserving agent employed is a base which produces a pH value of at least 8 in a 5% strength aqueous solution, or is a discharge reserving agent based on sulphites which contains an alkali metal sulphite or an alkali metal bisulphite in combination with an alkali metal carbonate or bicarbonate and, optionally, an aldehyde, and which, optionally contains a nonionic detergent, and if the abovementioned reactive dyestuffs which are dischargeable to white are present, the discharge reserving agent based on sulphites is employed, the improvement which comprises employing as the dischargeable disperse dyestuffs, dyestuffs having the formula I

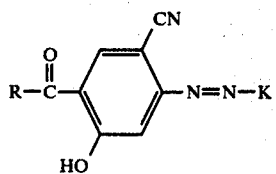 (I)

in which R is optionally substituted alkyl having 1 to 8 carbon atoms, optionally substituted alkoxy having 1 to 8 C atoms, and K is the radical of a coupling component of the benzene, naphthalene, pyridine, benzpyridine, diazole, thiazole, indole, carbazole, oxazole or diazine series or the series of enolisable 1,3-dicarbonyl compounds, the molecule of which dyestuffs contains not more than one esterified carboxyl group.

2. In the process of claim 1, the improvement that dischargeable disperse dyestuffs are employed having the formula I wherein R is alkyl having 1 to 4 C atoms, substituted alkyl having 1 to 4 C atoms, alkoxy having 1 to 4 C atoms and substituted alkoxy having 1 to 4 C atoms.

3. In the process of claim 1, the improvement that dischargeable disperse dyestuffs of the formula I are employed wherein R is alkyl or alkoxy each having 1 to 8 C atoms; alkyl or alkoxy having 1 to 8 C atoms monosubstituted or disubstituted by a substituent selected from the group consisting of chlorine, bromine, cyano, hydroxyl, alkoxy having 1 to 4 C atoms, alkeneoxy having 3 or 4 C atoms, hydroxyalkoxy having 2 to 4 C atoms, alkoxyalkoxy having a total of 3 to 8 C atoms, alkylcarbonyloxy having 2 to 4 atoms, benzoyloxy, substituted benzoyloxy, phenyl, substituted phenyl, phenoxy, substituted phenoxy; alkyl or alkoxy each having 1 to 8 C atoms being disubstituted by two substituents of the group defined before and carrying an OH group as third substituent.

4. In the process of claim 1, the improvement that dischargeable disperse dyestuffs of the formula I are employed wherein K is the radical of an aniline derivative of the formula

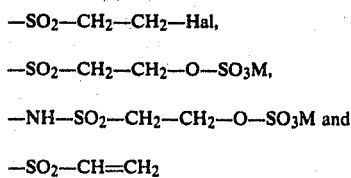

where R¹ is hydrogen, alkyl or alkenyl and R² is alkyl, alkenyl, cycloalkyl, phenyl, alkylcarbonyl, benzoyl, alkylsulphonyl or phenylsulphonyl, and in which the N-alkyl, N-alkenyl, N-cycloalkyl, N-phenyl, N-acyl, N-alkylsulphonyl and N-phenylsulphonyl radical are unsubstituted or substituted and in which the nucleus is unsubstituted or monosubstituted or polysubstituted by one or several substituents selected from the group consisting of alkyl having 1 to 4 C atoms, substituted alkyl having 1 to 4 C atoms, alkoxy having 1 to 4 C atoms, substituted alkoxy having 1 to 4 C atoms, alkeneoxy having 3 or 4 C atoms, phenoxy, substituted phenoxy, phenyl, substituted phenyl, fluorine, chlorine, bromine, alkylcarbonylamino, substituted alkylcarbonylamino, benzoylamino, substituted benzoylamino, alkenylcarbonylamino, alkylsulphonylamino, substituted alkylsulphonylamino, phenylsulphonylamino, substituted phenylsulphonylamino, N-alkyl-N-alkylsulphonylamino or N-alkyl-N-phenylsulphonylamino, substituted N-alkyl-N-alkylsulphonylamino or N-alkyl-N-phenylsulphonylamino, alkoxycarbonylamino, substituted alkoxycarbonylamino, alkeneoxycarbonylamino, cycloalkoxycarbonylamino or phenoxycarbonylamino, alkylaminocarbonylamino, substituted alkylaminocarbonylamino, alkenylaminocarbonylamino, cycloalkylaminocarbonylamino, phenylaminocarbonylamino and hydroxyl, or is a phenol in which the nucleus is unsubstituted or substituted by alkyl having 1 to 4 C atoms, alkylcarbonylamino or benzoylamino, substituted alkylcarbonylamino or benzoylamino or K is the radical of a 1-naphthylamine or 2-naphthylamine of the formula

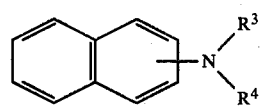

wherein R³ is hydrogen, alkyl and alkenyl and R⁴ is alkyl, alkenyl, cycloalkyl, phenyl, alkylcarbonyl, benzoyl, alkylsulphonyl or phenylsulphonyl, in which the N-alkyl or N-phenyl radicals are unsubstituted or substituted and in which the nucleus is unsubstituted or substituted by a substituent selected from the group consisting of alkyl having 1 to 4 C atoms, alkoxy having 1 to 4 C atoms, chlorine, bromine, aminosulphonyl, N-monoalkyl-substituted aminosulphonyl or N,N-dialkyl-substituted aminosulphonyl, the alkyl radicals in turn, independently of one another, being unsubstituted, monosubstituted or polysubstituted; or of a 1-naphthol or 2-naphthol in which the nucleus is unsubstituted or substituted by aminocarbonyl, monoalkylaminocarbonyl, dialkylaminocarbonyl or phenylaminocarbonyl the alkyl and phenyl groups of which are, independently of one another, unsubstituted or substituted, alkoxycarbonyl, substituted alkoxycarbonyl, alkeneoxycarbonyl, cycloalkoxycarbonyl or phenoxycarbonyl, amino, alkylcarbonylamino, substituted alkylcarbonylamino, alkenylcarbonylamino, benzoylamino, substituted benzoylamino, alkylsulphonylamino, substituted alkylsulphonylamino, phenylsulphonylamino, substituted phenylsulphonylamino, alkyl having 1 to 4 C atoms, alkoxy having 1 to 4 C atoms, chlorine or bromine, aminosulphonyl and monoalkylaminosulphonyl and dialkylaminosulphonyl in which the alkyl radicals, independently of one another, are unsubstituted or substituted, or K is a radical of a pyridone of the formula II

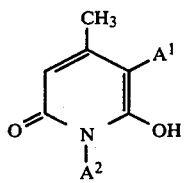
(II)

in which $A^1$ is cyano, nitro, aminocarbonyl, substituted amino carbonyl or hydrogen and $A^2$ is hydrogen, amino, substituted amino, or alkyl having 1 to 8 C atoms, substituted alkyl having 1 to 8 C atoms, or K is a radical of a pyridine derivative of the formula III

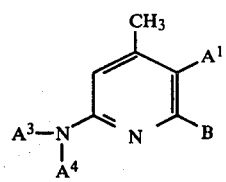
(III)

in which $A^3$ and $A^4$ are hydrogen or, independently of one another are alkyl having 1 to 8 C atoms, substituted alkyl having 1 to 8 C atoms, alkenyl having 3 to 5 C atoms or cycloalkyl having 5 or 6 C atoms and B is $NA^5A^6$ or alkoxy or alkylthio having 1 to 8 C atoms or substituted alkoxy or alkylthio having 1 to 8 C atoms and $A^5$ and $A^6$ independently of one another are hydrogen, or alkyl having 1 to 8 C atoms, substituted alkyl having 1 to 8 C atoms, alkenyl having 3 to 5 C atoms or cycloalkyl having 5 or 6 C atoms and A has the meanings mentioned above, or K is a radical of a pyridine derivative of the formula IV

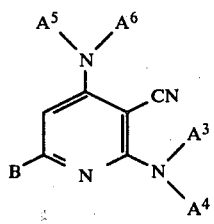
(IV)

in which $A^3$ to $A^6$ and B have the meanings mentioned above, or of an aminoquinoline, N-monoalkylaminoquinoline, N-monoalkenylaminoquinoline, N,N-dialkylaminoquinoline or N,N-dialkenylaminoquinoline in which the alkyl or alkenyl radical is unsubstituted or substituted, and N-cycloalkylaminoquinoline, N-phenylaminoquinoline, hydroxyquinoline and hydroxyisoquinoline and an N-alkylquinolone, N-alkenylquinolone, N-phenylquinolone, N-alkylisoquinolone, N-alkenylisoquinolone or N-phenylisoquinolone in which the alkyl radical is unsubstituted or substituted, or of a pyrazolone, aminopyrazole or N-alkylpyrazolone, N-phenylpyrazolone, N-alkylaminopyrazole and N-phenylaminopyrazole in which the alkyl or phenyl radical, respectively, is unsubstituted or substituted and in which the nucleus is unsubstituted or substituted by alkyl or phenyl or substituted alkyl or phenyl or by alkoxycarbonyl, or substituted alkoxycarbonyl, or of a 2-aminothiazole or N-monoalkylaminothiazole and N,N-dialkylaminothiazole in which the alkyl radicals independently of one another are unsubstituted or substituted and in which the nucleus is unsubstituted or substituted by a substituent selected from the group consisting of alkyl, alkenyl, cycloalkyl, aralkyl, aryl, heteroaryl, hydroxyl, amino, alkylcarbonylamino, benzoylamino, alkylsulphonylamino or phenylsulphonylamino which is unsubstituted or substituted or K is the radical of indole or an N-alkylindole in which the alkyl radical is unsubstituted or substituted and in which the nucleus is unsubstituted or substituted by alkyl, alkoxy, chlorine or bromine, or is the radical of carbazole or an N-alkylcarbazole in which the alkyl radical is unsubstituted or substituted and in which the nucleus is unsubstituted or substituted by hydroxyl, alkoxy, chlorine or bromine, or is the radical of hydroxyisooxazole in which the nucleus is unsubstituted or substituted by alkyl, substituted alkyl, phenyl, alkoxy, substituted alkoxy, chlorine or bromine, or is the radical of an N,N-dialkylbarbituric acid, N,N-diarylbarbituric acid or N-alkyl-N-arylbarbituric acid, or is the radical of acetoacetanilide in which the phenyl radical is unsubstituted or substituted by chlorine, bromine, methyl, hydroxy or methoxy.

5. In the process of claim 1, the improvement that dischargeable disperse dyestuffs of the formula I are employed wherein K is the radical of a coupling component of the aniline, 6-hydroxypyrid-2-one, aminopyridine, 2-naphthol, 1-naphthylamine, 2-aminothiazole, indole or carbazole series.

6. In the process of claim 1, the improvement that dischargeable disperse dyestuffs of the formula I are employed where in the the alkyl radicals present in $R^1$, $R^2$ and $A^3$ to $A^6$ of the coupling components K contain 1 to 8 C atoms, the alkenyl radicals contain 3 to 5 C atoms and the cycloalkyl radicals contain 5 or 6 C atoms and the aryl radicals are phenyl or naphthyl radicals.

7. In the process of claim 1, the improvement that dischargeable disperse dyestuffs of the formula I are employed wherein the alkyl radicals of the coupling components are unsubstituted or substituted by a substituent selected from the group consisting of hydroxy, alkoxy having 1 to 4 C atoms, alkenyloxy having 3 to 5 C atoms, phenoxy, substituted phenoxy, cycloalkoxy having 5 or 6 C atoms, hydroxyalkoxy, alkylcarbonyloxyalkoxy and phenoxyalkoxy having 2 to 4 C atoms in the alkoxy radical and in the alkylcarbonyl radical, alkoxyalkoxy having 3 to 8 C atoms, hydroxyalkoxyalkoxy, alkylcarbonyloxyalkoxyalkoxy and phenoxyalkoxyalkoxy having 4 to 12 C atoms in the alkoxyalkoxy radical and 2 to 4 C atoms in the alkylcarbonyl radical; alkoxyalkoxyalkoxy having 5 to 16 C atoms; alkylcarbonyloxy having 2 to 4 C atoms; alkylcarbonyloxy having 2 to 4 C atoms in the alkyl group substituted by hydroxyl, chlorine, bromine, alkoxy having 1 to 4 C atoms or phenoxy and benzoyloxy and substituted benzoyloxy; alkoxycarbonyloxy having 1 to 4 C-atoms in the alkoxygroups, alkoxycarbonyloxy having 1 to 4 C atoms in the alkoxy group substituted by hydroxy, chlorine, bromine, alkoxy having 1 to 4 C atoms, or phenoxy; alkeneoxycarbonyloxy having 3 to 5 C atoms in the alkeneoxy group; cycloalkoxycarbonyloxy having 5 or 6 C atoms in the cycloalkoxy group; phenoxycarbonyloxy, substituted phenoxycarbonyloxy; monoalkylaminocarbonyloxy unsubstituted or substituted, by hydroxyl, chlorine, bromine, alkoxy having 1 to 4 C atoms or phenoxy and which has 1 to 8 C atoms in the alkylamino group; monoarylaminocarbonyloxy, substituted monoarylaminocarbonyloxy; phenyl, substituted phenyl; chlorine; bromine; and cyano, and in the event that R is alkyl or substituted alkyl, alkoxycarbonyl having 1 to 8 C atoms in the alkoxy group, which is unsubstituted or substituted; alkeneoxycarbonyl having 3 to 5 C atoms in the alkeneoxy group; cycloalkoxycarbonyl having 5 or 6 C atoms in the cycloalkyl group; and phenoxycarbonyl in which the phenoxy radical is unsubstituted or substituted, and the naphthyl or phenyl radicals are monosubstituted or disubstituted by fluorine, chlorine, bromine, trifluoromethyl, alkyl having 1 to 4 C atoms or alkoxy having 1 to 4 C atoms.

8. The textile material which has been coloured by the process of any one of claims 1 to 7.

* * * * *